(12) United States Patent
Shiraishi

(10) Patent No.: US 7,714,850 B2
(45) Date of Patent: May 11, 2010

(54) DISPLAY DEVICE AND DRIVING METHOD THEREOF

(75) Inventor: Tai Shiraishi, Yamatokoriyama (JP)

(73) Assignee: Sharp Kabushiki Kaisha, Osaka (JP)

( * ) Notice: Subject to any disclaimer, the term of this patent is extended or adjusted under 35 U.S.C. 154(b) by 998 days.

(21) Appl. No.: 11/190,808

(22) Filed: Jul. 28, 2005

(65) Prior Publication Data

US 2006/0022603 A1 Feb. 2, 2006

(30) Foreign Application Priority Data

Jul. 30, 2004 (JP) ............................. 2004-224814

(51) Int. Cl.
*G09G 5/00* (2006.01)
(52) U.S. Cl. ...................... 345/204; 345/205; 345/206; 345/209; 345/89
(58) Field of Classification Search ......... 345/204–206, 345/209, 89
See application file for complete search history.

(56) References Cited

U.S. PATENT DOCUMENTS

| 5,771,031 | A | 6/1998 | Kinoshita et al. |
| 6,072,456 | A | 6/2000 | Karube et al. |
| 6,177,917 | B1 | 1/2001 | Koizumi et al. |
| 6,388,651 | B1 | 5/2002 | Kinoshita et al. |
| 6,972,741 | B1 | 12/2005 | Isono et al. |
| 2001/0003447 | A1 | 6/2001 | Murai et al. |
| 2001/0035862 | A1 | 11/2001 | Nakamura et al. |
| 2002/0063671 | A1 | 5/2002 | Knapp |
| 2002/0140712 | A1 | 10/2002 | Ouchi et al. |
| 2003/0043100 | A1 | 3/2003 | Moon |
| 2004/0246278 | A1* | 12/2004 | Elliott ........................ 345/692 |
| 2006/0007069 | A1 | 1/2006 | Isono et al. |

FOREIGN PATENT DOCUMENTS

| JP | 5-35201 (A) | 2/1993 |
| JP | 5-35221 (A) | 2/1993 |
| JP | 07-152905 | 6/1995 |
| JP | 09-114423 | 5/1997 |
| JP | 09-171376 | 6/1997 |
| JP | 10-207434 | * 8/1998 |
| JP | 10-307567 | 11/1998 |

(Continued)

*Primary Examiner*—Richard Hjerpe
*Assistant Examiner*—Leonid Shapiro
(74) *Attorney, Agent, or Firm*—Harness, Dickey & Pierce, P.L.C.

(57) ABSTRACT

A display device includes a left and a right panel sections provided adjacently along a sequence of a plurality of data signal lines, and a plurality of source drivers which are provided along a sequence of the data signal lines and correspond to the panel sections. A controller sends data signals to the respective source drivers in parallel, and a start signal to one of the source drivers in each of the display panel. In each panel section, an operation of acquiring data signals sequentially shifts from the source driver having received the start signal to the next source driver. The controller sends the start signals to the two source drivers closest to a border between the two display regions, and rearranges an order of data signals, which are supplied to source drivers in one of the display regions, to be in line with an order of data signals which are supplied to the other one of the display regions.

10 Claims, 19 Drawing Sheets

FOREIGN PATENT DOCUMENTS

| | | |
|---|---|---|
| JP | 2001-166277 | 6/2001 |
| JP | 2003-75802 | 3/2003 |
| KR | 2003-0012302 | 2/2003 |
| TW | 394919 | 6/2000 |
| TW | 540027 | 7/2003 |

* cited by examiner

FIG. 1 (DUAL PORT INPUT, REGULAR SCANNING DRIVE)

(SINGLE PORT INPUT, REGULAR SCANNING DRIVE, DATA TRANSMISSION TIMING)

(SINGLE PORT INPUT, REVERSED SCANNING DRIVE, DATA TRANSMISSION TIMING)

(DUAL PORT INPUT, REGULAR SCANNING DRIVE, DATA TRANSFER)

(DUAL PORT INPUT, REVERSED SCANNING DRIVE, DATA TRANSMISSION)

FIG. 10
WRITING 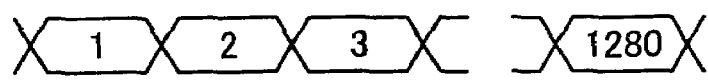
READING
REGULAR
DISPLAY
Data L 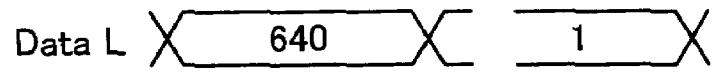
Data R 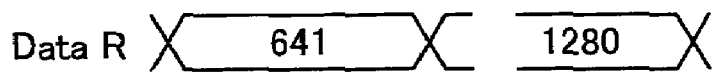
READING
LEFT-AND-RIGHT
INVERTED DISPLAY
Data L 
Data R 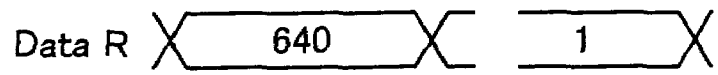

(DUAL PORT INPUT, REGULAR SCANNING DRIVE, DATA TRANSFER)

FIG. 17 (DUAL PORT INPUT, REVERSED SCANNING DRIVE, DATA TRANSFER)

(SINGLE PORT INPUT, REGULAR SCANNING DRIVE, DATA TRANSMISSION TIMING)

(SINGLE PORT INPUT, REVERSED SCANNING DRIVE, DATA TRANSMISSION TIMING)

DISPLAY DEVICE AND DRIVING METHOD THEREOF

This Nonprovisional application claims priority under 35 U.S.C. §119(a) on Patent Application No. 2004/224814 filed in Japan on Jul. 30, 2004, the entire contents of which are hereby incorporated by reference.

FIELD OF THE INVENTION

The present invention relates to a display device such as flat panel display devices typified by liquid crystal display devices, and its driving method.

BACKGROUND OF THE INVENTION

Currently, flat panel displays such as liquid crystal display devices or the like have been used for display devices of television sets, personal computers, or the like. The following describes conventional arts of a liquid crystal display device representing flat panel displays as an example. Note that, in the following description, data1, data2, data3 . . . are display data to be respectively written in pixel1, pixel2, pixel3 . . . on a single horizontal line of the liquid crystal display panel in regular display mode, assuming that the pixel1, pixel2, pixel3 . . . are aligned from the left edge to the right edge.

FIG. 11 is a schematic view of an active matrix type liquid crystal display device. As shown in FIG. 11, the liquid crystal display device has a liquid crystal display panel 101, in which a plurality of source bus lines 102 and gate bus lines 103 are provided in a matrix fashion. The source bus lines 102 are connected to a source driver SD, and the gate bus lines 103 are connected to a gate driver GD. The source driver SD is provided along a direction orthogonal to the source bus lines 102 of the liquid crystal display panel 101. The gate driver GD is provided along a direction orthogonal to the gate bus lines 103. The source driver SD and the gate driver GD are operated under control of signals from a controller 106.

At respective intersections of the source bus lines 102 and the gate bus lines 103, TFTs 108 are provided. The source, gate, and drain of each TFT 108 are connected to the source bus line 102, the gate bus line 103, and pixel electrode 109, respectively. The pixel electrodes 109 are connected to opposing electrodes Com through liquid crystal capacities Clc.

In such a liquid crystal display device, using a line-sequential drive, the source driver SD provides data signals to the respective source bus lines 102 simultaneously, and the gate driver GD selects the gate bus lines 103 sequentially. Accordingly, the TFTs 108 connected to the selected gate bus lines 103 (in a selection period) are turned on, so that plural data signals of the source bus lines 102 are written into the pixel electrodes 109 through the TFTs 108. The written data signals are retained until next data signals are written into the pixel electrodes 109, thereby realizing desired display image on the liquid crystal display panel 101.

Next described is a signal transmitting system between the controller 106 and the source drivers SD in the liquid crystal display device.

FIG. 12 illustrates a structure of the liquid crystal display device having a horizontal resolution of 640 dots, for example. That is, there are 640 pixels on one horizontal line. Note that, the gate driver GD is omitted for simplification in FIG. 12. In the following description, each single pixel includes a total of three (red, green, and blue) picture elements.

As shown in FIG. 12, the actual liquid crystal display device has a plurality of source drivers SD, to which the source bus lines 102 are evenly connected. Here, five source drivers SD101 through SD105 are provided. Each of the source drivers SD101 through SD105 is connected to a bundle of 384 source bus lines 102.

The controller 106 sends not only a transmission clock and display data (Data), but also a start pulse SP (Start Pulse), a latch strobe LS (Latch Strobe), and a scanning direction signal DIR. The start pulse SP specifies a starting position of display data. The latch strobe LS is used for latching display data at the respective source drivers SD101 through SD105 simultaneously. The scanning direction signal DIR specifies a scanning direction of the source drivers SD101 through SD105.

The source drivers SD101 through SD105 send display data to the source bus lines 102, through internal flip flop circuits. Such driving circuits are disclosed in Japanese Laid-Open Patent Publication No. 35201/1993 (Tokukaihei 5-35201, publication date: Feb. 21, 1993), for example. Further, the transmission clock is used for setting timings for operating the flip flop circuits, and its frequency is increased in a case of high-definition display. Regarding this, the source drivers SD described later are the same.

Among the signals, only the start pulse SP is sent to a single source driver SD exclusively, while the other signals are commonly sent to all the source drivers SD101 to SD105 via connected buses. That is, a start pulse SP is sent from the controller 106 to a source driver SD provided at an edge of the liquid crystal display panel 101. Then, the start pulse SP is sent from the respective source drivers SD to their following source drivers SD sequentially. Afterwards, a source driver SD provided at another edge of the liquid crystal display panel 101 sends a start pulse SP to the controller 106.

The start pulses SP are supplied as above, due to the following reasons. That is, although sets of display data are commonly sent to all the source drivers SD101 through SD105 via connected buses, the respective source drivers SD101 through SD105 are required to acquire only corresponding display data. Thus, in order to identify display data corresponding to the respective source drivers SD101 through SD105, a start pulse SP is sent as described above.

More specifically, immediately after receiving a start pulse SP (SP1) from the controller 106, the source driver SD 101 acquires required numbers of display data (for first 128 pixels: display data for pixel1 through pixel128) from the display data sent from the controller 106, and then sends a start pulse SP (SP12) for the next source driver SD102. In a similar manner, immediately after receiving the start pulse SP, the source driver SD102 acquires display data for next 128 pixels (display data for pixel129 through pixel256), and then sends a start pulse SP (SP23) to the source driver SD103 of the next stage. In such a manner, the source drivers SD103, SD104, and SD105 acquire display data sequentially. Finally, the controller 106 sends a latch strobe LS for latching data to the respective source drivers SD101 through SD 105, so as to finish sending data of one horizontal line to the source drivers SD101 through SD105. When receiving latch strobes LS, the respective source drivers SD101 through SD105 output voltages corresponding to incoming data to the liquid crystal display panel 101. This operation is repeated for each horizontal line, so that display for one frame is carried out on the liquid crystal display panel 101.

Further, the scanning direction signal DIR, which is sent from the controller 106 commonly to the respective source drivers SD101 through SD105, specifies a shifting direction of the source drivers SD acquiring display data, that is, the scanning direction signal DIR specifies a scanning direction. In the case described above, the scanning direction signal DIR specifies left-to-right scanning (scanning direction from the source drivers SD101 toward SD105: DIR=L). Therefore, the operation of acquiring sets of display data corresponding to the source drivers SD101 through SD105 shifts from the source driver SD101 toward SD105. Further, sets of display data of each horizontal line are sent to the source drivers SD101 through SD105 in accordance with a sequence of data1, data2, . . . , data640, so that regular display having no left-and-right inversion is carried out.

On the contrary, FIG. 13 illustrates a case of carrying out left-and-right inverted display. Unlike regular display, a start pulse SP is first sent from the controller 106 to the source driver SD105. Then, a start pulse SP is sequentially sent from the SD105 to its following source driver SD104, and then from the SD104 to its following SD103. Finally, the source driver SD101 sends a start pulse SP to the controller 106. Further, the scanning direction signal DIR specifies right-to-left scanning (scanning direction from the source driver SD105 toward SD101: DIR=H). Therefore, in a manner opposite to regular display, the operation of acquiring sets of display data corresponding to the source drivers SD101 through SD105 shifts from the source driver 105 toward 101. Further, sets of display data of a single horizontal line are, in a manner similar to regular display, sent to the source drivers SD105 through SD101 in accordance with a sequence of data1, data2, . . . , data640, so that left-and-right inverted display is properly carried out.

As described above, in the conventional liquid crystal display device having a left-and-right inversion function, a start pulse SP can be sent to either one of the source drivers SD101 and SD105 provided at the left and right edges of the liquid crystal display panel 101.

Note that, left-and-right inverted display is used for viewing a reflected image of the liquid crystal display device on a mirror. It is also used for utilizing some visual characteristics of a liquid crystal panel which has different visual characteristics in vertical direction, for example, by reversing its normal settings.

As shown in FIG. 14, a large liquid crystal display device is typically driven in a dual port input by splitting a screen into left and right sections. For example, in a liquid crystal display device having 1280 pixels on a single horizontal line, a screen is split into a left screen having 640 pixels (pixel1 through pixel640) and a right screen having 640 pixels (pixel640 through pixel1280) on a single horizontal line. Each of these two screens is simultaneously driven by a signal prepared for each screen.

More specifically, the liquid crystal display device shown in FIG. 14 has a liquid crystal display panel 111 including a left panel section 111a and a right panel section 111b. The left panel section 111a having source drivers SD111 through SD115 corresponding to the left screen and the right panel section 111b having source drivers SD116 through SD120 corresponding to the right screen.

When such a liquid crystal display device carries out regular display, start pulses SP (SP1 and SP6) are sent to source drivers SD111 and SD116, which are provided at respective left edges of the left panel section 111a and the right panel section 111b. Based on the start pulses SP, the source drivers SD111 and SD116 acquire display data of pixel1 through pixel128 and display data of pixel641 through pixel768, respectively, from data sent from the controller 116. On completion of acquiring the display data, the source drivers SD111 and SD116 send start pulses SP (SP12 and SP67) for the respective source drivers SD112 and SD117. As with the above, subsequent source drivers SD acquire display data, so that sending data of one horizontal line to the source drivers SD111 through SD120 finishes. This operation is repeated for each horizontal line, so that display for one frame is carried out on the liquid crystal display panel 111.

In the above operation, the scanning direction signal DIR, which is sent from the controller 116 commonly to the respective source drivers SD111 through SD120, specifies left-to-right scanning (DIR=L). Further, sets of display data for each horizontal line are sent to the source drivers SD111 through SD115 and SD116 through SD120 in accordance with a sequence of data1, data2, . . . data640, and data641, data642, . . . , data1280, so that regular display having no left-and-right inversion is carried out.

FIG. 15 is a timing chart of the signals for the above operations. In FIG. 15, SP1 is a start pulse SP sent from the controller 116 to the source driver SD111. CKL is a transmission clock, DataL is display data, and LSL is a latch strobe LS, all of which are sent from the controller 116 to the source drivers SD111 through SD115 of the left panel section 111a. In a similar manner, SP6 is a start pulse SP sent from the controller 116 to the source driver SD116. CKR is a transmission clock, DataR is display data, and LSR is a latch strobe LS, all of which are sent from the controller 116 to the source drivers SD116 through SD120 in the right panel section 111b.

On the contrary, FIG. 16 illustrates a case of carrying out left-and-right inverted display. Unlike regular display, start pulses SP (SP5 and SP10) are first sent from the controller 116 to the source drivers SD115 and SD120 which are provided at respective right edges of the left panel section 111a and the right panel section 111b. Afterwards, the start pulses SP are sequentially sent from the source drivers SD115 and SD120 to their following source drivers SD114 and SD119, respectively. Further, the scanning direction signal DIR specifies right-to-left scanning (DIR=H). Therefore, in a manner opposite to regular display, the operation of acquiring sets of display data corresponding to the source drivers SD111 through SD115 and SD116 through SD120 shifts from the source drivers SD115 and SD120 toward SD111 and SD116. Further, in a manner similar to regular display, sets of display data of each horizontal line are sent to the source drivers SD111 through SD115 and SD116 through SD120, respectively, in accordance with a sequence of data1, data2, . . . , data640 and data 641, data642, . . . , data1280, so that normal left-and-right inverted display is carried out.

FIG. 17 is a timing chart of the signals for the above operation. In FIG. 17, codes of the respective signals indicate as described above.

In a liquid crystal display device shown in FIG. 14, phase relations between transmission clocks and start pulses (SP1 and SP6) are important for transmissions toward the source drivers SD111 and SD116. Also, phase relations between transmission clocks and start pulses (SP5 and SP10) are important for transmissions toward the source drivers SD115 and SD120.

As described above, the transmission clock is sent commonly to the source drivers SD111 through SD115, and the transmission clock is commonly sent to the source drivers SD116 through SD120, both via connected buses. On the other hand, a start pulse SP is first sent to the source drivers SD111 and SD116 (regular display) or the source drivers SD115 and SD120 (left-and-right inverted display). Then, the start pulse SP is passed to their following source drivers sequentially. In such a manner, a condition for sending transmission clocks is different from those of the start pulse. Due to less burdens of transmission channels, the start pulse is transmitted faster than the transmission clocks.

Such a state is described with reference to FIGS. 18 and 19. FIG. 18 illustrates a phase relation between a transmission clock and a start pulse SP (SP1) which are sent to the source driver SD101, when the liquid crystal display device shown in FIG. 12 carries out regular display. This phase relation is equivalent to a phase relation between a transmission clock and a start pulse SP which are sent to the source driver SD116 in regular display mode or to the source driver SD115 in left-and-right inverted display mode in the liquid crystal display device shown in FIG. 14. Also, FIG. 19 illustrates a phase relation in the liquid crystal display device shown in FIG. 12, which is a relation between a transmission clock and a start pulse SP (SP5) which are sent to the source driver SD105 in left-and-right inverted display mode (FIG. 13). The phase relation is equivalent to a phase relation between a transmission clock and a start pulse SP which are sent to the source driver SD111 in regular display mode or to the source driver SD120 in left-and-right inverted display mode (FIG. 16) in the liquid crystal display device shown in FIG. 14.

In a state shown in FIG. 18, the phase relation between a transmission clock and a start pulse SP is appropriate, so that a balance between a Tsetup1 period and a Thold1 period in flip flop circuits forming the source drivers SD is properly maintained. On the other hand, in a state shown in FIG. 19, the phase relation between a transmission clock and a start pulse SP becomes imbalanced. A balance between a Tsetup5 period and a Thold5 period is not maintained having a shorter Thold5 period, because a start pulse SP is transmitted earlier than a transmission clock. Note that, the Tsetup and the Thold indicate conditions of timings when the flip flop circuits acquire data. The operation will not be ensured without securing predetermined periods, respectively.

FIG. 12 illustrates the liquid crystal display device with no two-split drive. In order to obtain a left-and-right inversion function, the liquid crystal display device shown in FIG. 12 requires an appropriate phase difference between transmission clocks and start pulses SP in both of the source drivers SD101 and SD105. Further, the liquid crystal display device with a two-split drive shown in FIG. 14 requires an appropriate phase difference between transmission clocks and start pulses SP in both of the source drivers SD111 and SD116, even when left-and-right inversion function is not used (i.e. in regular display mode). That is, the larger the phase difference is, the smaller margins of timing between sending transmission clocks and start pulses SP become in the liquid crystal display device.

On the other hand, FIG. 19 illustrates retardation from the appropriate state shown in FIG. 18. The phase retardation increases as the transmission length of a signal increases. As a result, it becomes hard to adjust timings, thereby restricting a transmission frequency. This problem is prominent in larger liquid crystal display devices having a long distance for transmitting signals, or in liquid crystal display devices carrying out high-definition display at a high transmission frequency.

More specifically, the following occurs in the liquid crystal display device with a two-split drive shown in FIG. 14. In regular display mode, since a transmission distance is shortest to the source driver SD116 and longest to the source driver SD111, it is hard to adjust timings between a transmission clock and a start pulse SP in the source driver SD111. Also, in left-and-right inverted display mode, since a transmission distance is shortest to the SD115 and longest to the SD120, it is hard to adjust timings between a transmission clock and a start pulse SP in the source driver SD120. In this way, the liquid crystal display device with a two-split drive shown in FIG. 14 has difficulties in adjusting timings for sending transmission clocks and start pulses, because start pulses are first sent from the controller 116 to the closest source driver SD and the farthest source driver SD.

Note that, Japanese Laid-Open Patent Publication No. 35221/1993 Tokukaihei 5-35221 (publication date: Feb. 12, 1993) discloses a structure of a dot-sequential drive, and a technique for preventing vertical stripes from appearing in adjacent display regions when carrying out a two-split drive for a display screen. According to the structure described in this publication, the operation of acquiring data signals shifts from driving circuits provided at both ends toward driving circuits in a center region, sequentially. However, this publication describes neither start pulses SP nor the problem due to retardation of start pulses, which serves no solution for the problem.

SUMMARY OF THE INVENTION

Under two-split drive structure, an object of the present invention is to provide a display device which easily adjusts timings for sending signals to source drivers SD and a driving method thereof.

To attain the foregoing object, the display device of the present invention includes a first display region; a second display region; a plurality of driving circuits which are provided along a sequence of data signal lines and correspond to the display regions; and a controlling circuit sending data signals to the respective driving circuits in parallel while sending a start signal to one of the driving circuits in each of the display regions, in each of the display regions an operation of acquiring data signals corresponding to driving circuits sequentially shifting from said one of the driving circuits having received the start signal to a driving circuit next to said one of the driving circuits, the first display region and the second display region being provided adjacently along a sequence of a plurality of data signal lines, the controlling circuit sending the start signals to the two driving circuits closest to a border between the two display regions, and at a time of supplying the data signals, the controlling circuit rearranging an order of data signals, which are supplied to at least one of the display regions, to be in line with an order of data signals which are supplied to the other one of the display regions.

Further, a driving method for a display device includes a first display region, a second display region, and a plurality of driving circuits which are provided along a sequence of data signal lines and correspond to the display regions, the first display region and the second display region being provided adjacently along a sequence of a plurality of the data signal lines, the driving circuits receiving data signals in parallel and one of the driving circuits in each of the display regions receiving a start signal, in each of the display regions an operation of acquiring data signals corresponding to driving circuits sequentially shifting from said one of the driving circuits having received the start signals to a driving circuit next to said one of the driving circuits, the start signals being sent to the two driving circuits closest to a border between the two display regions, and an order of the data signals supplied to at least one of the display regions being rearranged to be in line with an order of data signals which are supplied to the other one of the display regions.

According to the arrangement, start signals are sent from the controlling circuit to driving circuits, which are closest to the controlling circuit, in the first and the second display regions, respectively. For example, in the first and the second display regions which are provided adjacently, start signals are sent to a rightmost driving circuit in the left-side first display region and to a leftmost driving circuit in the right-side second display region. After the start signals are received, the operation of acquiring sets of data signals corresponding to driving circuits sequentially shifts from the source drivers having received the start signals toward adjacent driving circuits in the respective display regions. That is, in the left-side first display region, a rightmost driving circuit first acquires data signals, and then driving circuits on its left acquire data signals sequentially. In a similar manner, in the right-side second display region, a leftmost driving circuit first acquires data signals, and then driving circuits on its right acquire data signals sequentially.

Further, the controlling circuit supplies data signals to a driving circuit in at least one of the display regions by rearranging an order of data signals to be in line with an order of data signals supplied to the other one of the display regions. As an example, assume that the first and the second display regions are provided adjacently. When carrying out regular display with no left-and-right inversion, the controlling circuit supplies data signals to driving circuits in the left-side first display region by rearranging data in a reversed order. This makes it possible to carry out normal regular display even when the two driving circuits start acquiring data signals.

Start signals can be sent to the two driving circuits through a shortest transmission distance, because the start signals are sent to the two driving circuits closest to the border between the first and the second display regions, the two driving circuits adjacently provided in a center region. This enables suppressing the amount of retardation of start pulses and equalizing the amount of retardation of start signals sent to the two driving circuits. Thus, it is possible to facilitate adjusting a phase between other controlling signals and start signals, which are sent to the driving circuits. That is, timings for sending signals to driving circuits can be easily adjusted under the two-split drive structure.

For a fuller understanding of the nature and advantages of the invention, reference should be made to the ensuring detailed description taken in conjunction with the accompanying drawings.

BRIEF DESCRIPTION OF THE DRAWINGS

FIG. 10 is an explanatory view showing operations of writing and reading display data in and from a line memory in the structure shown in FIG. 9.

DESCRIPTION OF THE EMBODIMENTS

First Embodiment

Figure 11:
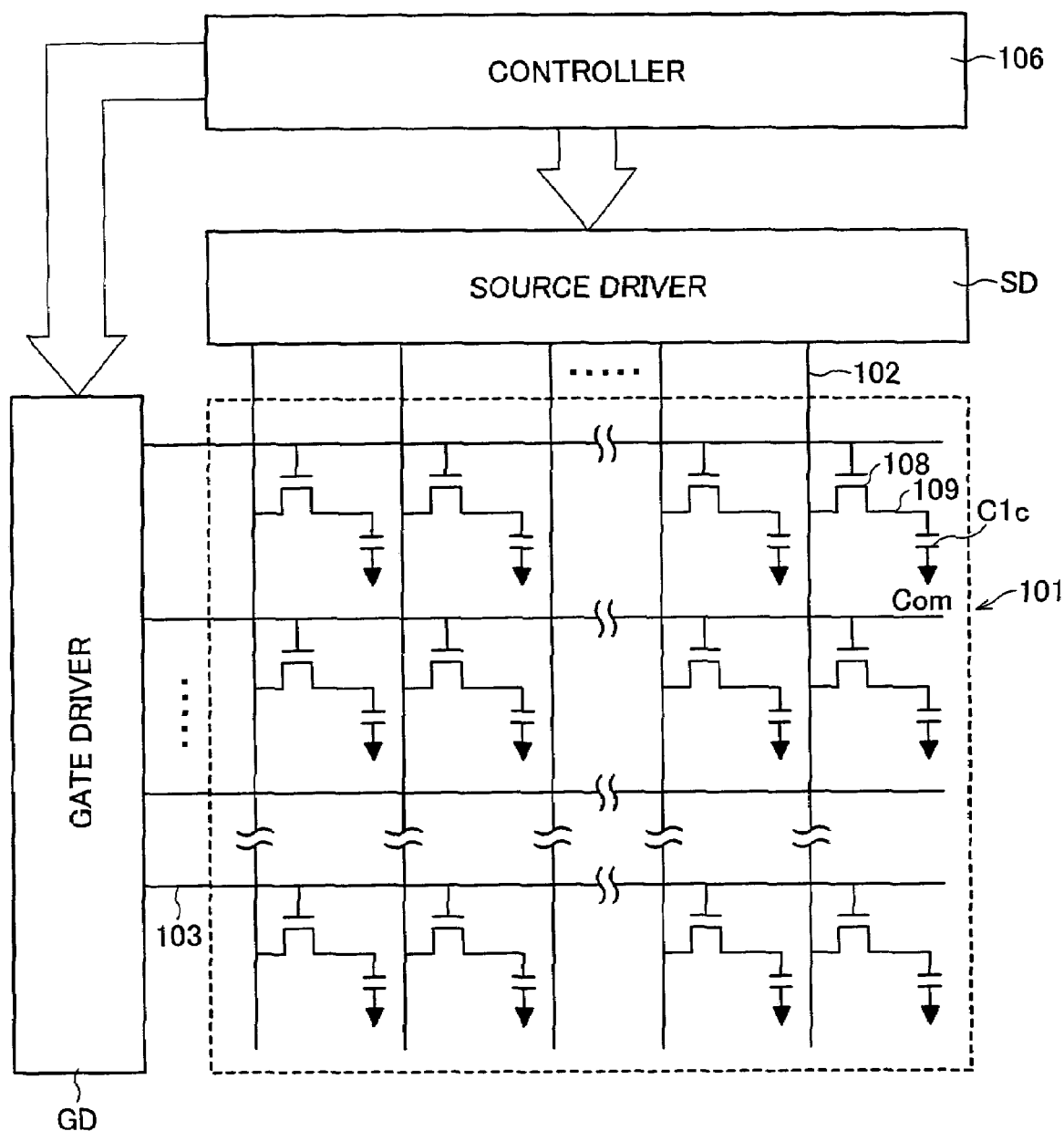
FIG. 11 is a schematic view of a conventional liquid crystal display device.
Figure 12:
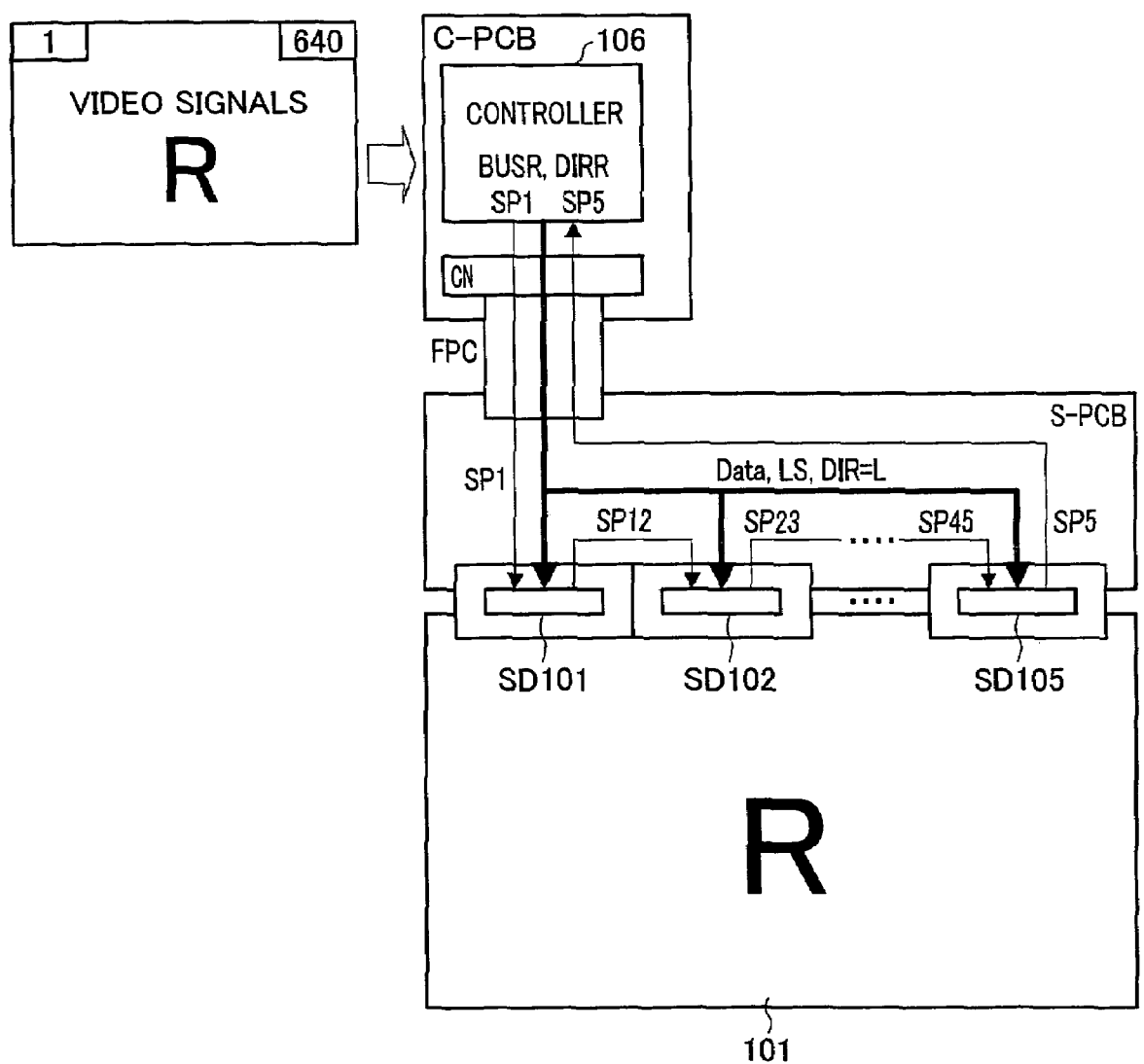
FIG. 12 is a front view schematically illustrating a conventional liquid crystal display device with no two-split drive when carrying out regular display.
Figure 13:
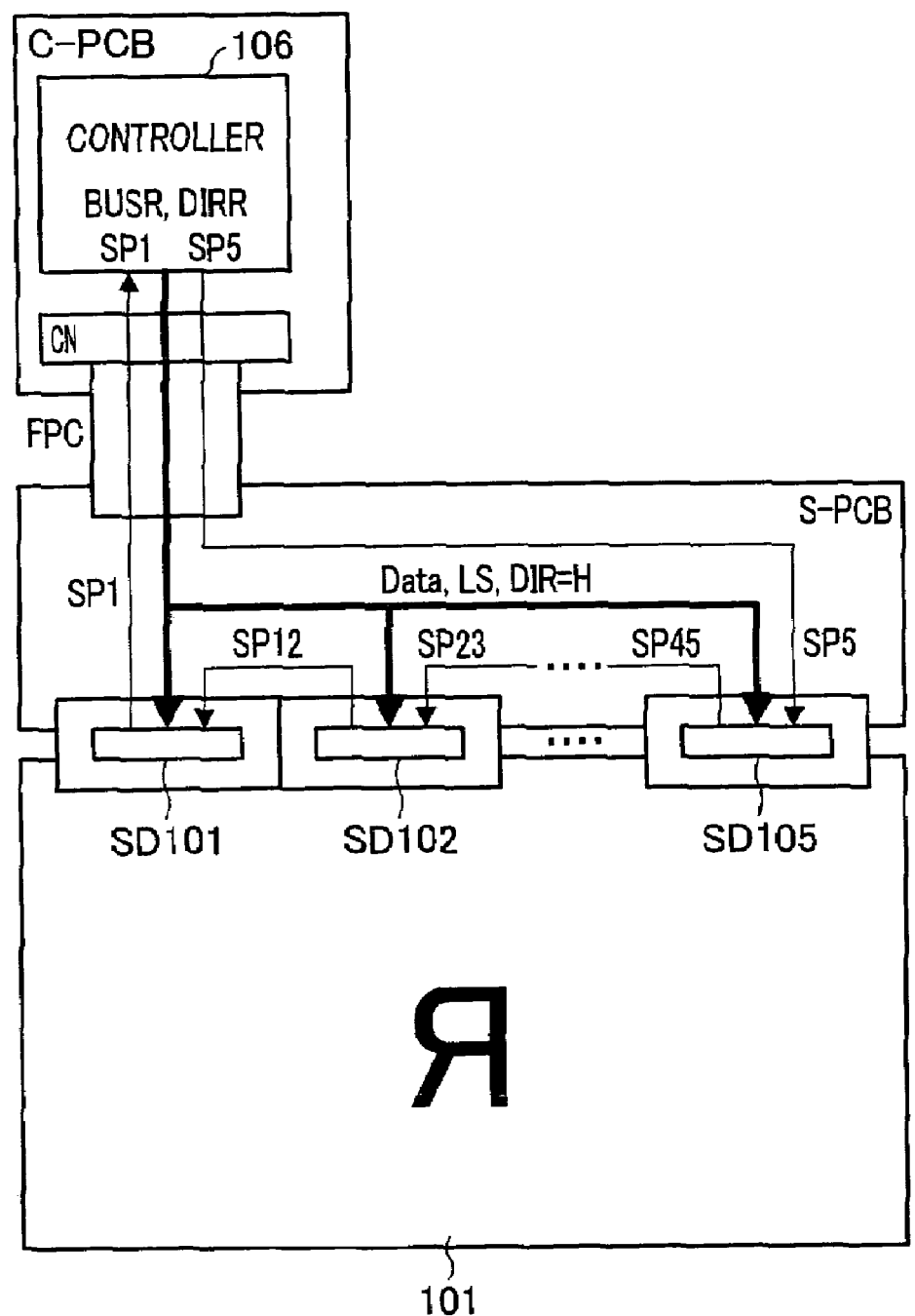
FIG. 13 is a front view schematically illustrating the liquid crystal display device shown in FIG. 12 when carrying out left-and-right inverted display.
Figure 14:
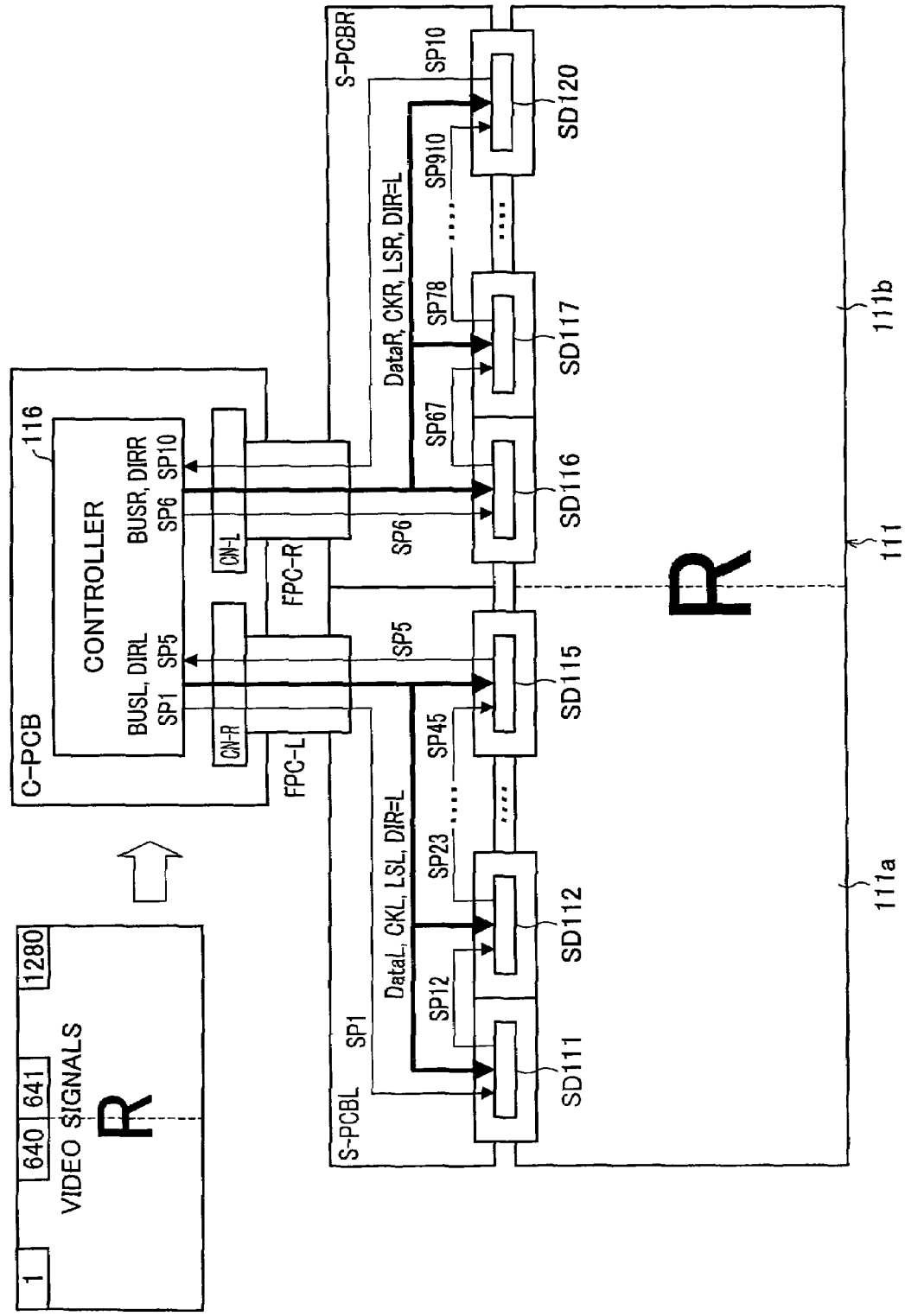
FIG. 14 is a front view schematically illustrating a conventional liquid crystal display device with a two-split drive when carrying out regular display.
Figure 15:
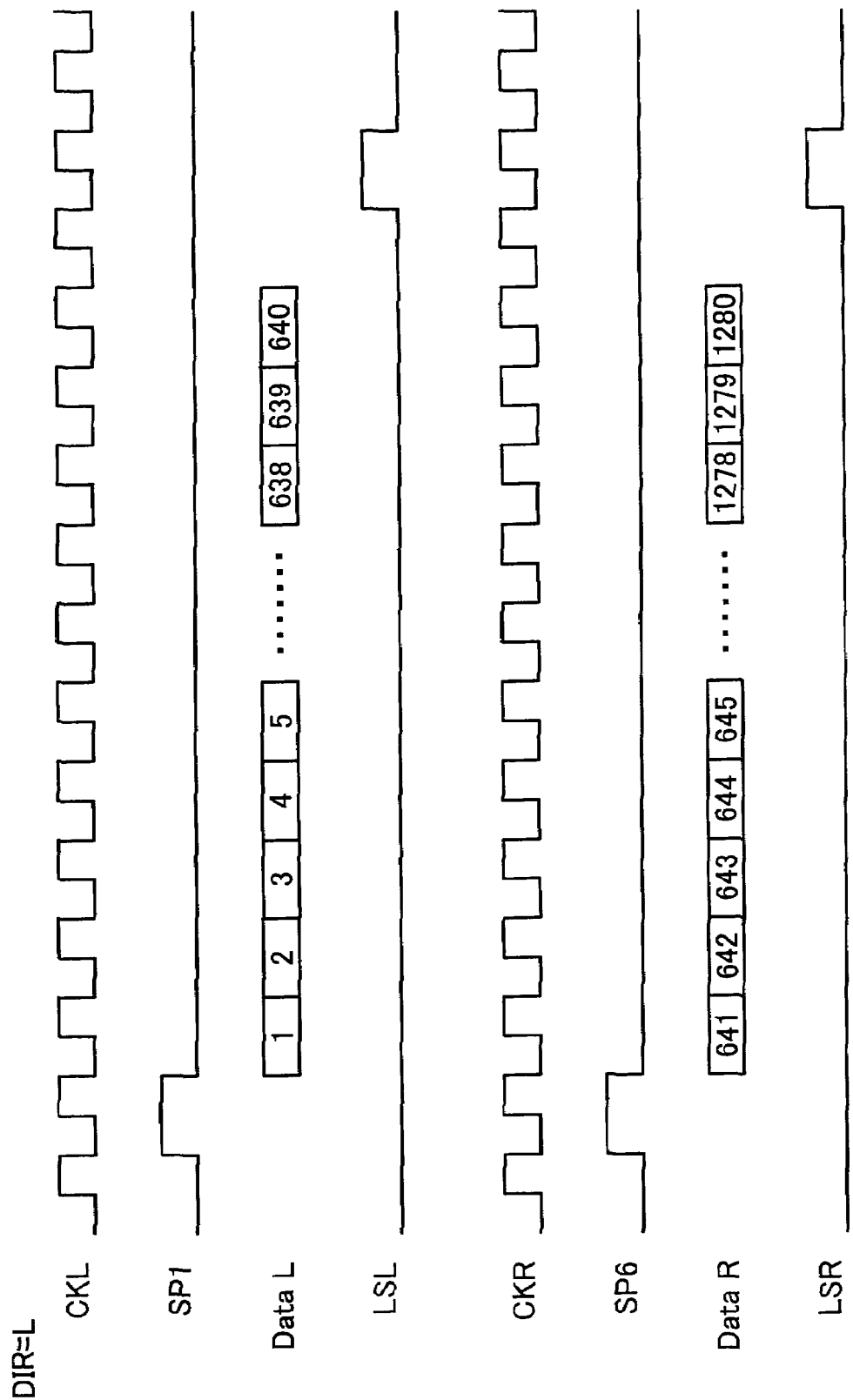
FIG. 15 is a timing chart showing signals from different sections and sequential orders of display data sent to the source drivers in the liquid crystal display device which carries out regular display as shown in FIG. 14.
Figure 16:
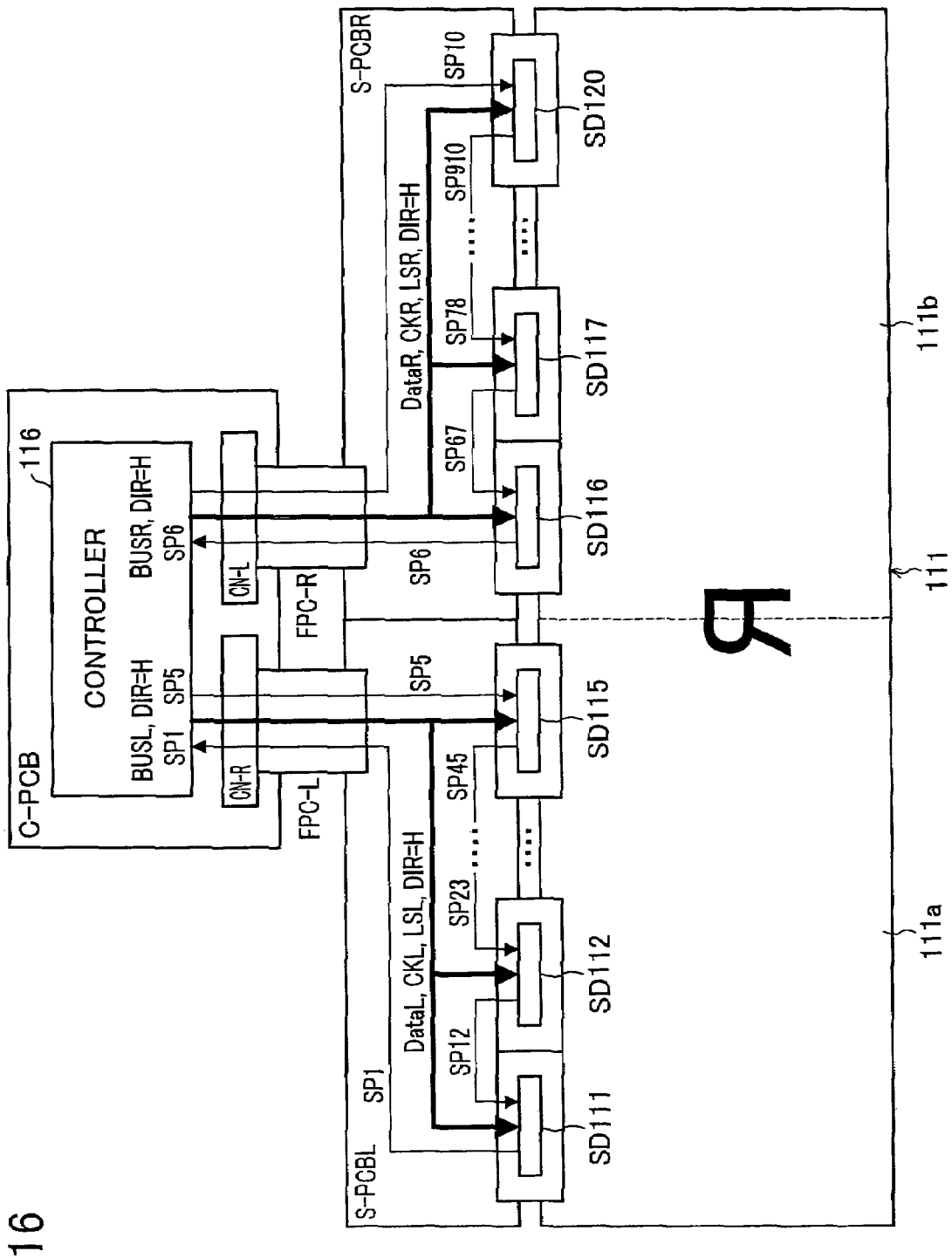
FIG. 16 is a front view schematically illustrating the liquid crystal display device shown in FIG. 14 when carrying out left-and-right inverted display.
Figure 17:
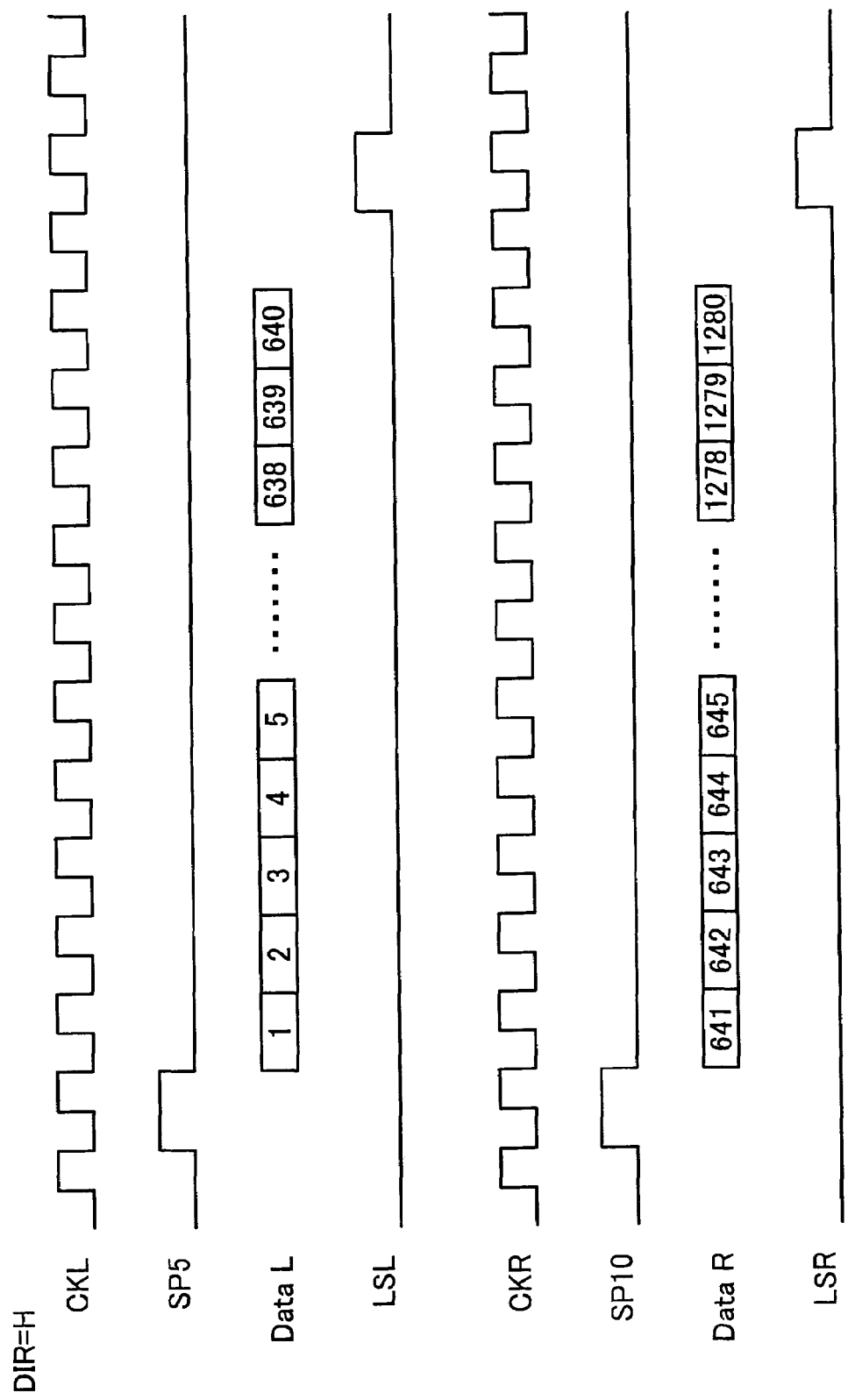
FIG. 17 is a timing chart showing signals from different sections and display data sent to the source drivers in the liquid crystal display device which carries out left-and-right inverted display shown in FIG. 16.
Figure 18:
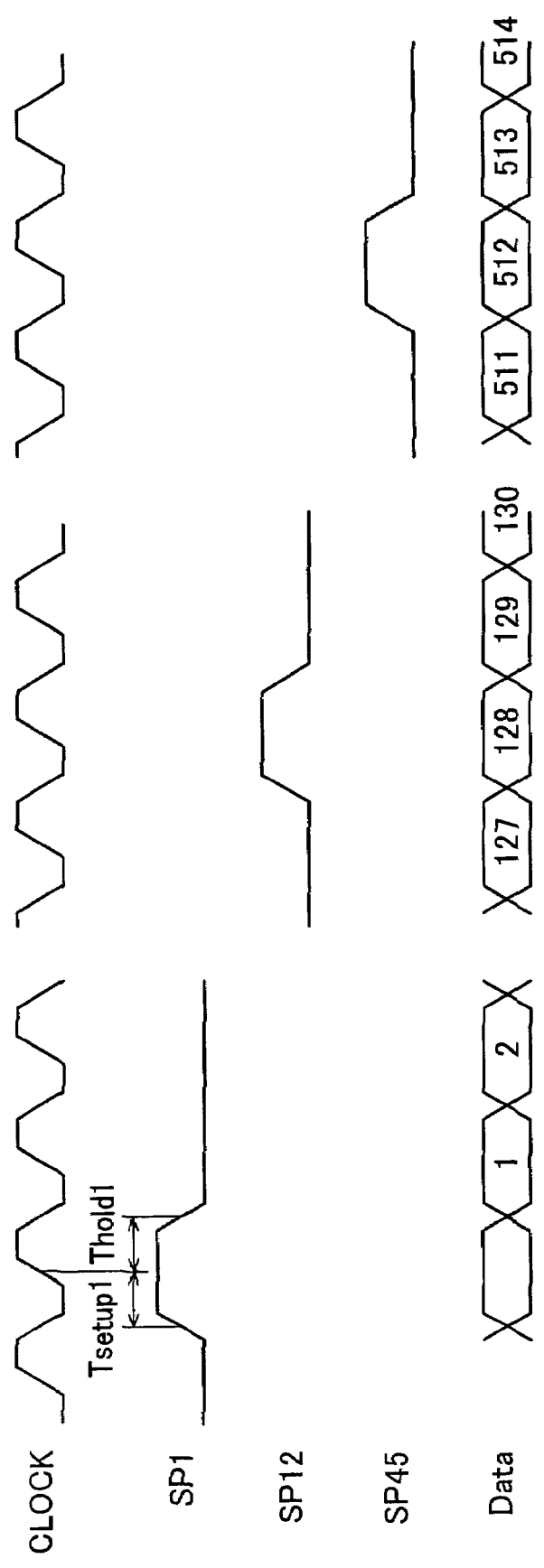
FIG. 18 is a timing chart showing phase differences among signals in the liquid crystal display device which carries out regular display shown in FIG. 12.
Figure 19:
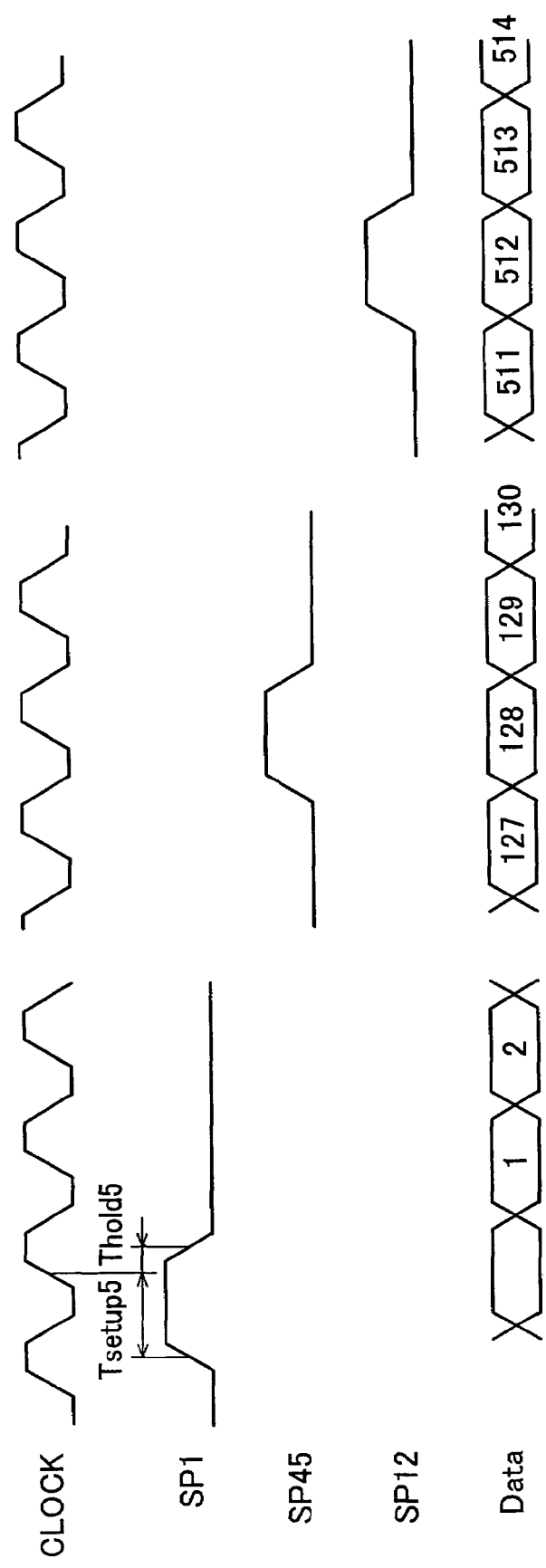
FIG. 19 is a timing chart showing phase differences among signals in the liquid crystal display device which carries out left-and-right inverted display shown in FIG. 13.

With reference to figures, the following describes one embodiment of the present invention. According to the arrangement of the present invention, an active matrix type liquid crystal display device (hereafter referred to as liquid crystal display device) is used as an example of a display device of the present invention. The structure of the liquid crystal display device is shown in FIG. 11.

With reference to FIGS. 2 through 5, a principle of the liquid crystal display device of the present embodiment is described.

Figure 2:
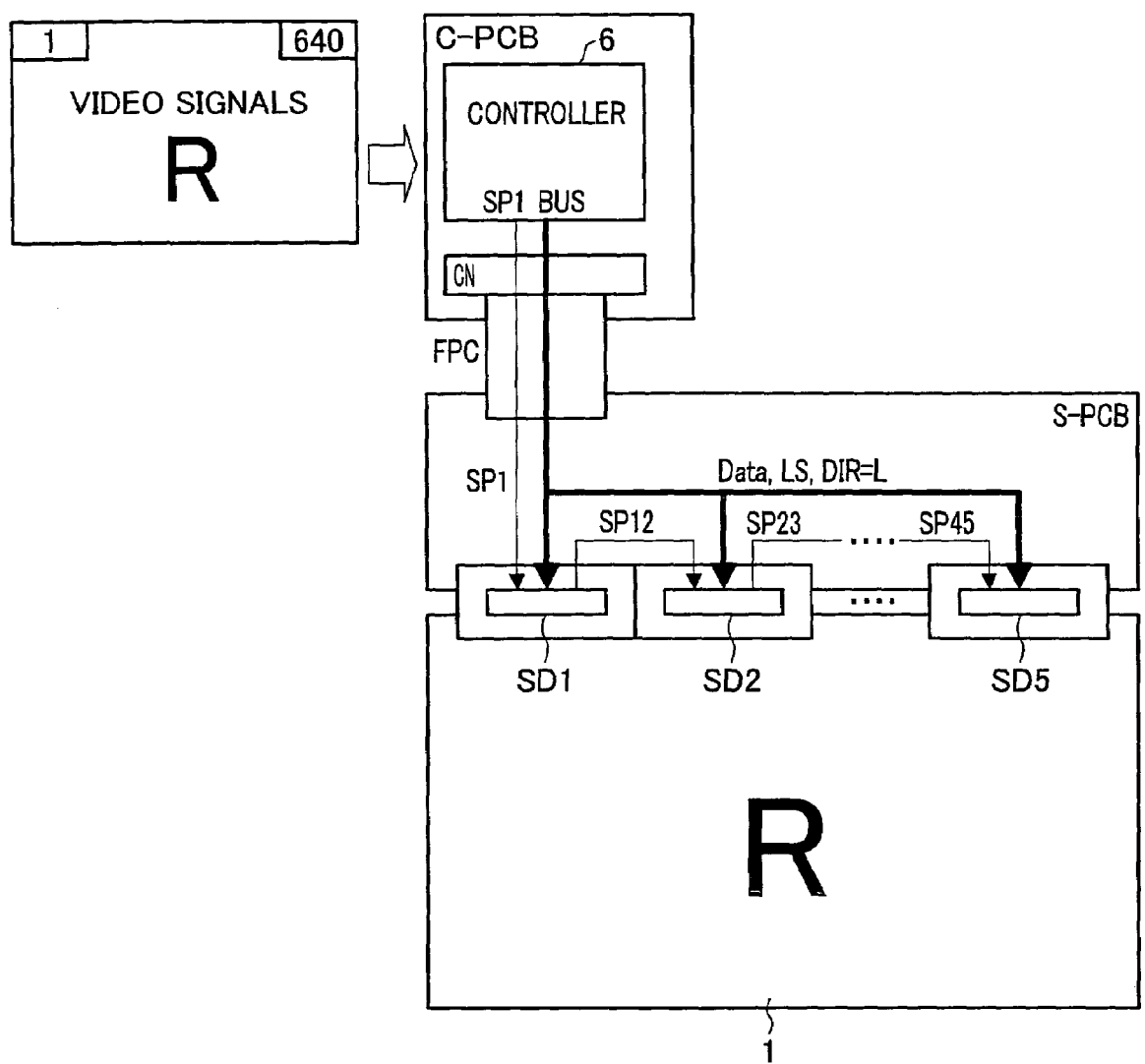
FIG. 2 is a front view schematically illustrating the liquid crystal display device with no two-split drive in regular display mode, which describes a principle of the liquid crystal display device shown in FIG. 1.

FIG. 2 illustrates a liquid crystal display device with no two-split drive. This liquid crystal display device includes a liquid crystal display panel 1 having a horizontal resolution of 640 dots, for example. That is, there are 640 pixels on one horizontal line. Note that, a gate driver is omitted for simplification in FIG. 2.

As shown in FIG. 2, the liquid crystal display device has a plurality of source drivers SD, to which source bus lines are evenly connected. Here, five source drivers SD1 through SD5 are provided. Each of the source drivers SD1 through SD5 is connected to a bundle of 384 source bus lines.

From a controller 6, not only a transmission clock and display data (Data), but also a start pulse SP (Start Pulse), a latch strobe LS (Latch Strobe), and a scanning direction signal DIR are sent. The start pulse SP specifies a starting position of display data. The latch strobe LS is used for latching display data in the respective source drivers SD1 through SD5 simultaneously. The scanning direction signal DIR specifies a scanning direction of the source drivers SD1 through SD5. The transmission clock functions as a control signal which sets timings for sending display data (data signals) to source bus lines.

Immediately after receiving the start pulse SP (SP1) from the controller 6, the source driver SD1 acquires required numbers of display data (first 128 pixels: display data for pixel1 through pixel128) from the display data sent from the controller 6, and then outputs a start pulse SP (SP12) for the next source driver SD2. In a similar manner, immediately after receiving the start pulse SP, the source driver SD2 acquires display data for next 128 pixels (display data for pixel129 through pixel256), and then outputs a start pulse SP (SP23) for the next source driver SD3. In such a manner, the source drivers SD3, SD4, and SD5 acquire display data sequentially. Finally, the controller 6 sends a latch strobe LS to the respective source drivers SD1 through SD5, so that sending data of one horizontal line to the source drivers SD1 through SD5 finishes. The respective source drivers SD1 through SD5 output, when receiving the latch strobe LS, voltages corresponding to incoming data to the liquid crystal display panel 1. This operation is repeated for each horizontal line, so that display for one frame is carried out on the liquid crystal display panel 1.

Further, the scanning direction signal DIR, which is sent from the controller 6 commonly to each of the source drivers SD1 through SD5, specifies left-to-right scanning (scanning direction from the source drivers SD1 to SD5: DIR=L). Therefore, the operation of acquiring sets of display data corresponding to the source drivers SD1 through SD5 shifts from the source driver SD1 toward SD5. Further, sets of display data of each horizontal line are sent to the source drivers SD1 through SD5 in accordance with a sequence of data1, data2, . . . , data640, so that regular display having no left-and-right inversion is carried out.

Figure 3:
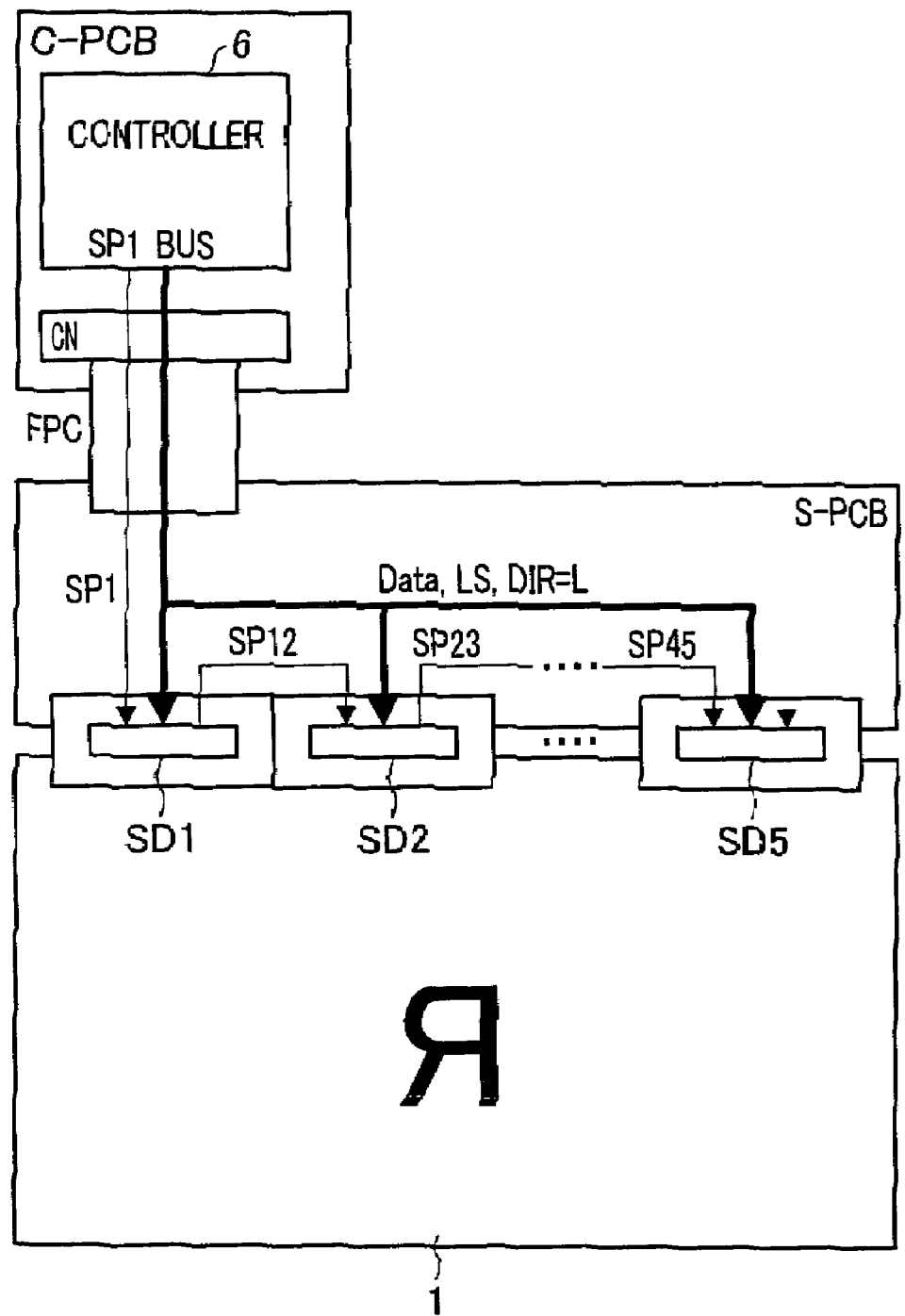
FIG. 3 is a front view schematically illustrating the liquid crystal display device shown in FIG. 2 when carrying out left-and-right inverted display.

FIG. 3 illustrates a case of carrying out left-and-right inverted display. In a manner similar to regular display, a start pulse SP is first sent from the controller 6 to the source driver SD1. Then, a start pulse SP is sequentially sent to the source drivers of the subsequent stages.

Further, in a manner similar to regular display, the scanning direction signal DIR specifies left to right scanning (scanning direction from the source driver SD1 to SD5: DIR=L). Therefore, in a manner similar to regular display, the operation of acquiring sets of display data corresponding to the source drivers SD1 through SD5 shifts from the source driver SD1 toward SD5. On the other hand, in a manner opposite to regular display, sets of display data of a single horizontal line are sent to the source drivers SD1 through SD5 in accordance with a sequence of data640, data639, . . . , data1, so that normal left-and-right inverted display is carried out.

According to the arrangement, in both regular display and left-and-right inverted display modes, a start pulse SP is sent from the controller 6 to the same source driver SD1, which is closest to the controller 6.

Figure 4:
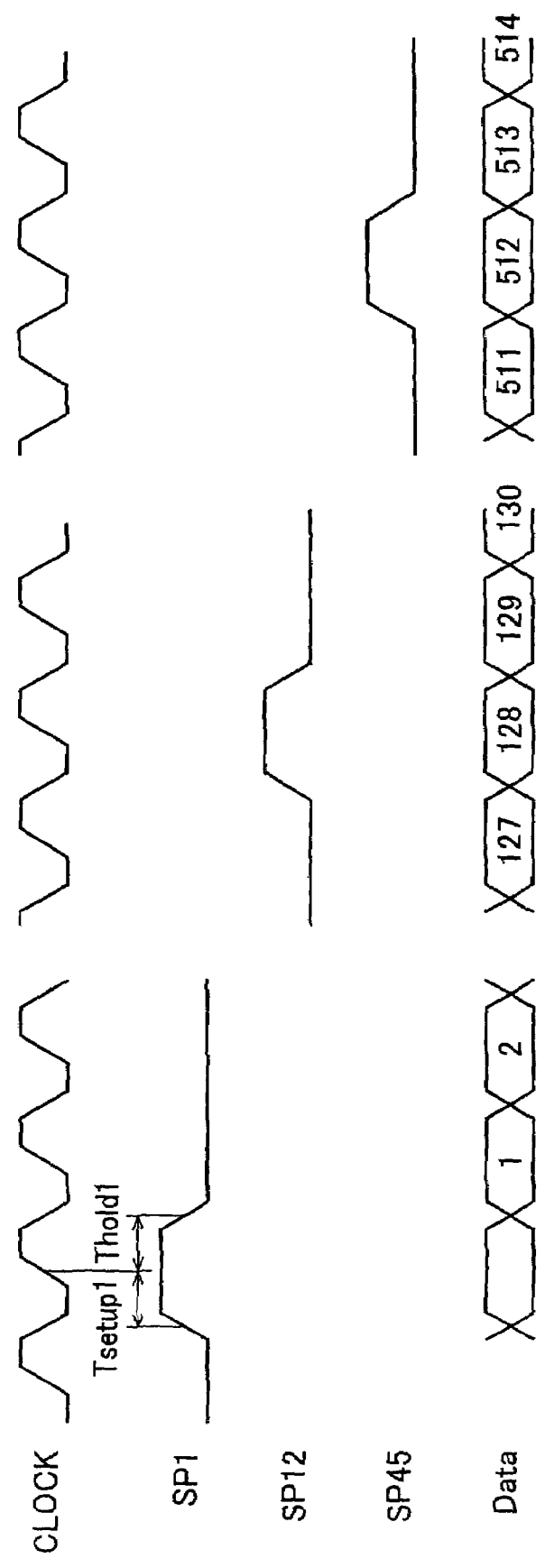
FIG. 4 is a timing chart showing a phase relation among signals in the liquid crystal display device which carries out regular display shown in FIG. 2.
Figure 5:
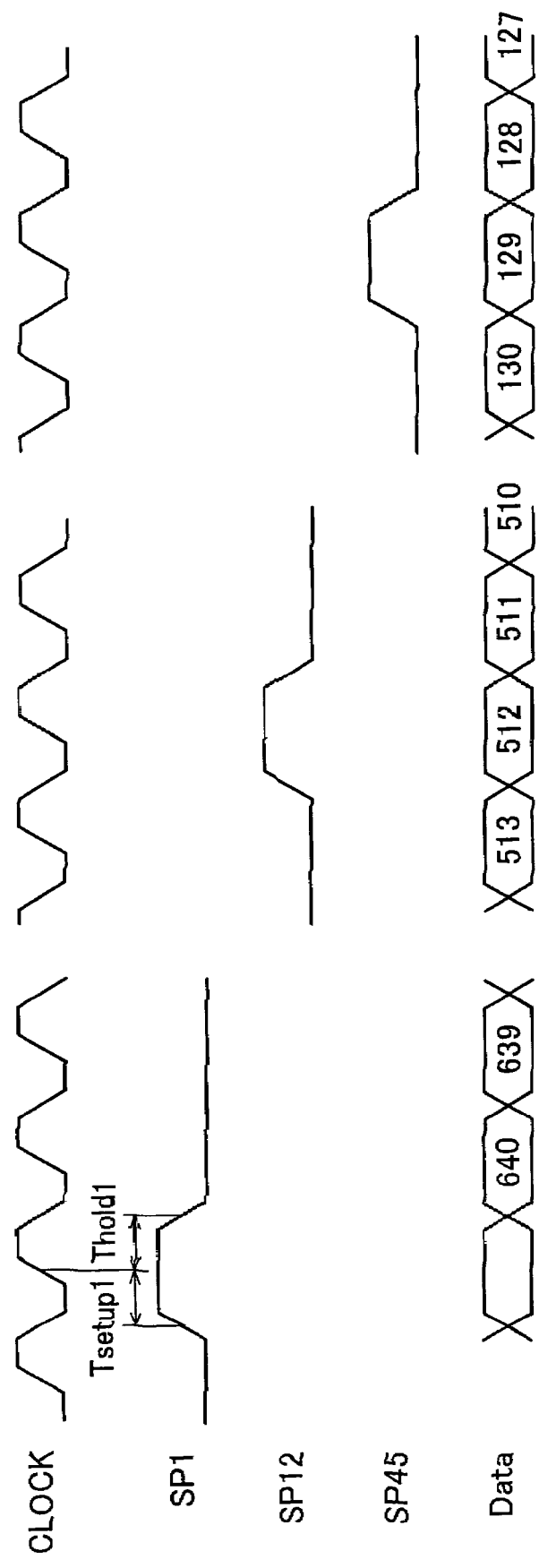
FIG. 5 is a timing chart showing a phase relation among signals in the liquid crystal display device which carries out left-and-right inverted display as shown in FIG. 3.

With reference to FIGS. 4 and 5, the above state is described. FIGS. 4 and 5 illustrate a phase relation between a transmission clock and a start pulse SP (SP1) which are sent to the source driver SD1 when regular display and left-and-right inverted display (FIG. 3) are carried out in the liquid crystal display device shown in FIG. 2.

In regular display mode shown in FIG. 4, the phase relation between the transmission clock and the start pulse SP is appropriate, so that a balance between a Tsetup1 period and a Thold1 period is appropriately maintained in flip flop circuits forming the source drivers SD. Also, sets of display data are sent to the source drivers SD1 through SD5 in accordance with a sequence of data1, data2, . . . , data640, respectively.

Similarly, in left-and-right inverted display mode shown in FIG. 5, the phase relation between the transmission clock and the start pulse SP is appropriate, so that a balance between the Tsetup1 period and the Thold1 period is appropriately maintained in flip flop circuits forming the source drivers SD. On the other hand, display data are sent to the source drivers SD1 through SD5 in accordance with a sequence of data640, data639, . . . , data1, respectively, which is a reversed order of the sequence in regular display mode.

In this way, according to the arrangement, timings for sending a transmission clock and a start pulse SP from the controller 6 can be easily adjusted in both regular display and left-and-right inverted display modes, because a start pulse SP is sent to the same source driver SD1, which is closest to the controller 6, in the both display modes.

Figure 1:
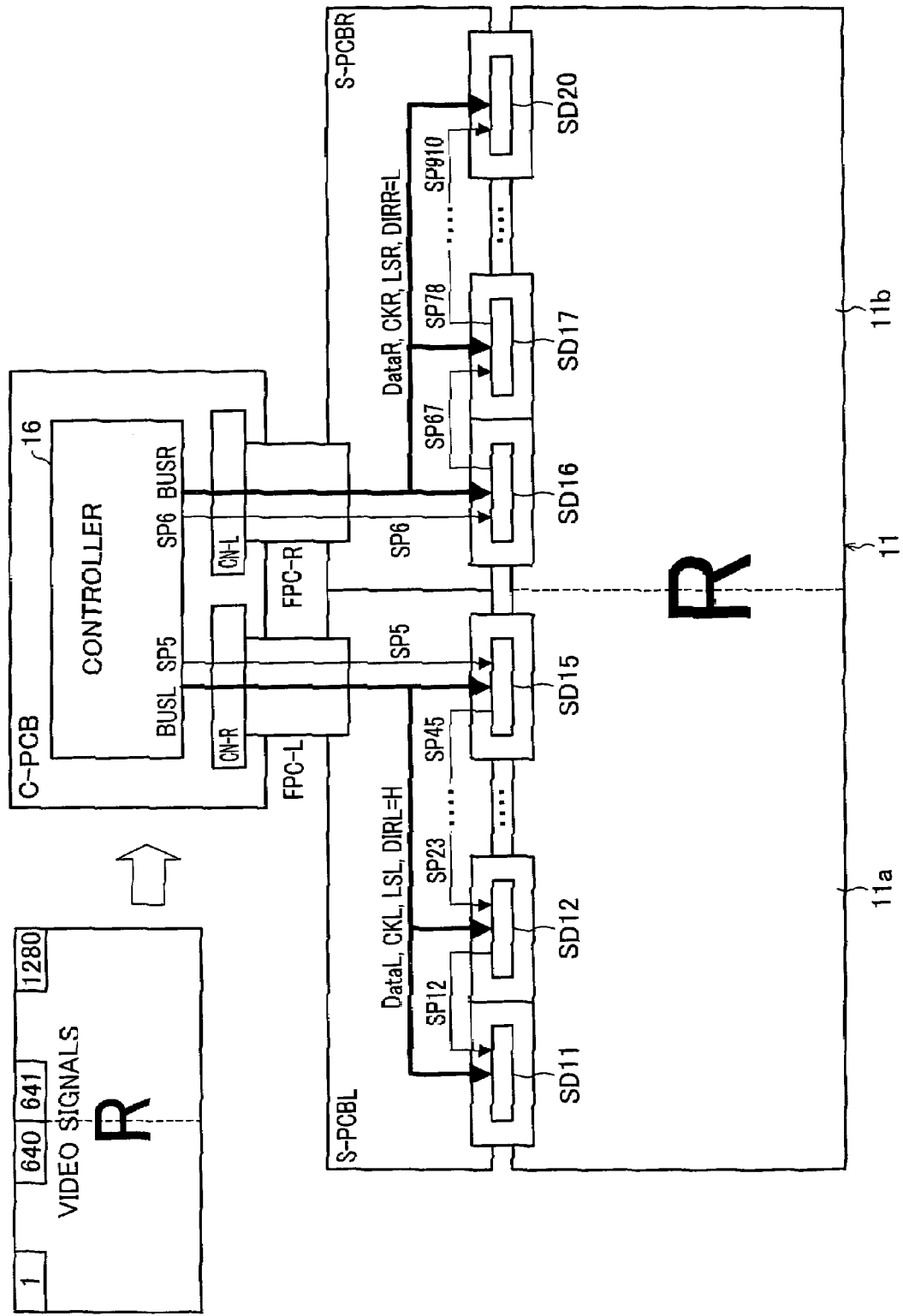
FIG. 1 is a front view schematically illustrating a liquid crystal display device with a two-split drive in regular display mode according to one embodiment of the present invention.

Next described is a liquid crystal display device of the present embodiment. As shown in FIG. 1, the liquid crystal display device of the present embodiment is driven in a dual port input by splitting a screen into left and right portions. The liquid crystal display device has, for example, 1280 pixels (pixel1, pixel2, . . . , pixel1280) on a single horizontal line from the left edge to the right edge, and a screen is split into a left screen having 640 pixels (pixel1 through pixel640) and a right screen having 640 pixels (pixel641 through pixel1280) on a single horizontal line. These two screens are driven by signals for the respective screens, simultaneously.

More specifically, the liquid crystal display device shown in FIG. 1 has a liquid crystal display panel 11 including a left panel section (first display region) 11a and a right panel section (second display region) 11b. The left panel section (first display region) 11a having source drivers (driving circuits) SD11 through SD15 and the right panel section (second display region) 11b having source drivers (driving circuits) SD16 through SD20 are prepared for the left screen and the right screen, respectively.

When such a liquid crystal display device carries out regular display, start pulses SP (SP5 and SP6) are sent from a controller 16 (controlling circuit) to the source drivers SD15 and SD16, which are closest to a border between the left panel section 11a and the right panel section 11b in the respective panel sections. Afterwards, in the left panel section 11a, the operation of acquiring sets of image data shifts from the rightmost source driver SD15 toward the leftmost source driver SD11, sequentially. Also, in the right panel section 11b, the operation of acquiring sets of display data shifts from the leftmost source driver SD16 toward the rightmost source driver SD20, sequentially.

That is, based on the start pulses SP, the source drivers SD15 and SD16 acquire display data of pixel640 through pixel512 (128 pixels) and display data of pixel641 through pixel768 (128 pixels), respectively, from data sent from the controller 16. On completion of acquiring the display data, the source drivers SD15 and SD16 send start pulses SP (SP45 and SP67) to their following source drivers SD14 and SD17. In a similar manner, subsequent source drivers SD acquire display data, so as to finish sending data of a single horizontal line through the source drivers SD11 to SD20. This operation is repeated for each horizontal line, so that display for one frame is carried out on the liquid crystal display panel 11.

In the above operations, a scanning direction signal DIRL, which is sent from the controller 16 commonly to the respective source drivers SD11 through SD15 in the left panel section 11a, specifies right-to-left scanning (DIRL=H), while a scanning direction signal DIRR, which is sent from the controller 16 commonly to the respective source drivers SD16 through SD20 in the right panel section 11b, specifies left-to-right scanning (DIRR=L).

Figure 6:
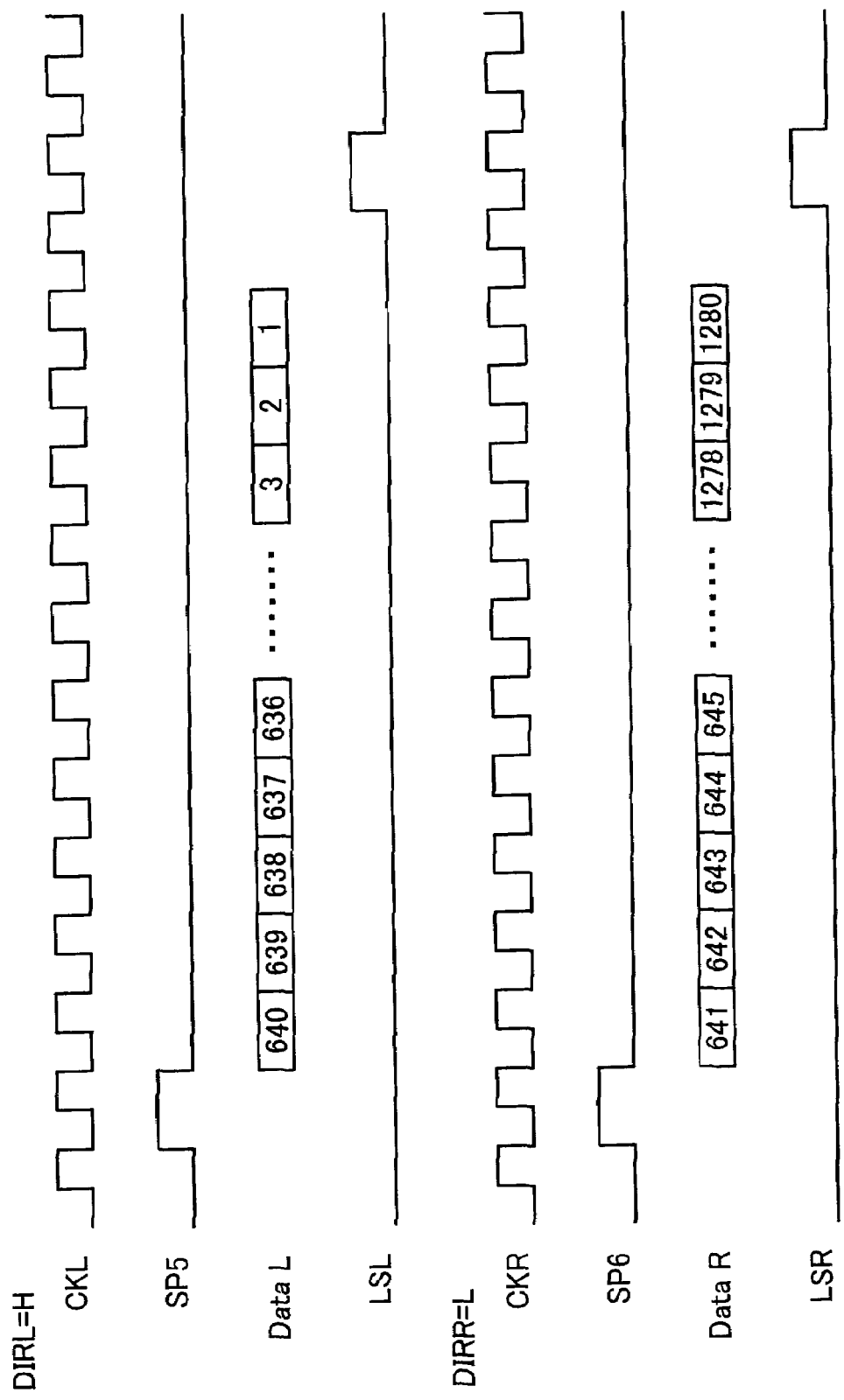
FIG. 6 is a timing chart showing signals from different sections and sequential orders of display data sent to source drivers in the liquid crystal display device which carries out regular display shown in FIG. 1.

Further, sets of display data for each horizontal line in the left panel section 11a are sent to the source drivers SD11 through SD15 in accordance with a sequence of data640, data639, . . . data1 (see FIG. 6). Sets of display data of each horizontal line in the right panel section 11b are sent to the source drivers SD16 through SD20, in accordance with a sequence of data641, data642, . . . , data1280 (see FIG. 6). This makes it possible to carry out regular display with no left-and-right inversion.

FIG. 6 is a timing chart of the signals for the regular display operation above. In FIG. 6, SP5 is a start pulse SP sent from the controller 16 to the source driver SD15. CKL is a transmission clock, DataL is display data, and LSL is a latch strobe LS, all of which are sent from the controller 16 to the source drivers SD11 through SD15 in the left panel section 11a. In a similar manner, SP6 is a start pulse SP sent from the controller 16 to the source driver SD16. CKR is a transmission clock, DataR is display data, and LSR is a latch strobe LS, all of which are sent from the controller 16 to the source drivers SD16 through SD20 in the right panel section 11b.

Figure 7:
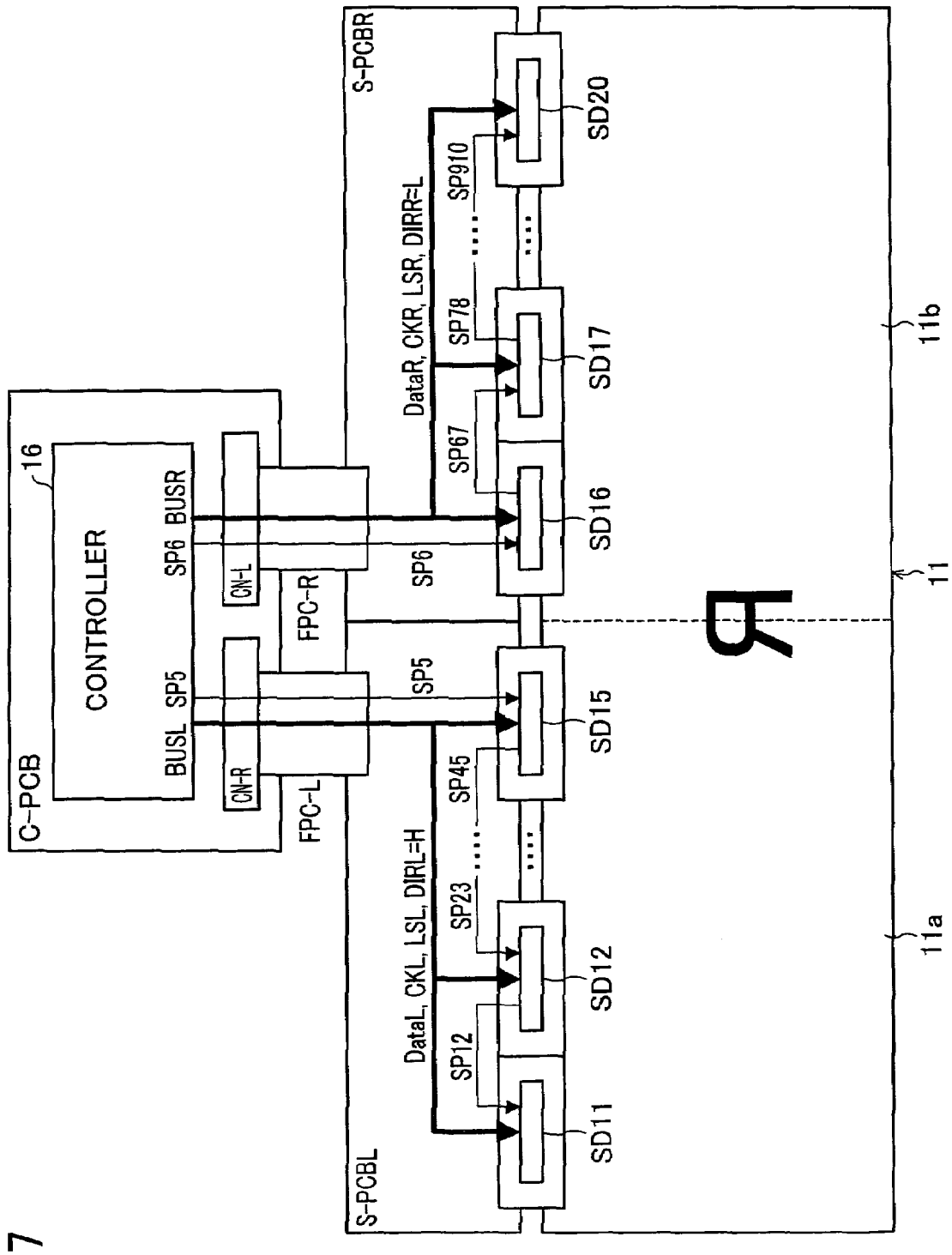
FIG. 7 is a front view schematically illustrating the liquid crystal display device shown in FIG. 1 when carrying out left-and-right inverted display.

FIG. 7 illustrates a case of carrying out left-and-right inverted display. In a manner similar to regular display, the start pulses SP (SP5 and SP6) are first sent from the controller 16 to the source drivers SD15 and SD16 in the left panel section 11a and the right panel section 11b, respectively. Afterwards, in the left panel section 11a, the operation of acquiring sets of display data shifts from the rightmost source driver SD15 toward the leftmost SD11, sequentially. Also, in the right panel section 11b, the operation of acquiring sets of display data shifts from the leftmost source driver SD16 toward the rightmost SD20, sequentially.

That is, based on the start pulses SP, the source drivers SD15 and SD16 acquire display data of pixel640 through pixel512 (128 pixels) and pixel641 through pixel768 (128 pixels), respectively, from the display data sent from the controller 16. On completion of acquiring data, the source drivers SD15 and SD16 send the start pulses SP (SP45 and SP67) to their following source drivers SD14 and SD17. In a similar manner, subsequent source drivers SD acquire display data, so that sending data of one horizontal line to the source drivers SD11 through SD20 finishes. This operation is repeated for each horizontal line, so that display of for one frame is carried out on the liquid crystal display panel 11.

In a manner similar to regular display, the scanning direction signal DIRL, which is sent from the controller 16 commonly to the respective source drivers SD11 through SD15 in the left panel section 11a, specifies right-to-left scanning (DIRL=H), while the scanning direction signal DIRR, which is sent from the controller 16 commonly to the respective source drivers SD16 through SD20 in the right panel section 11b, specifies left-to-right scanning (DIRR=L).

Figure 8:
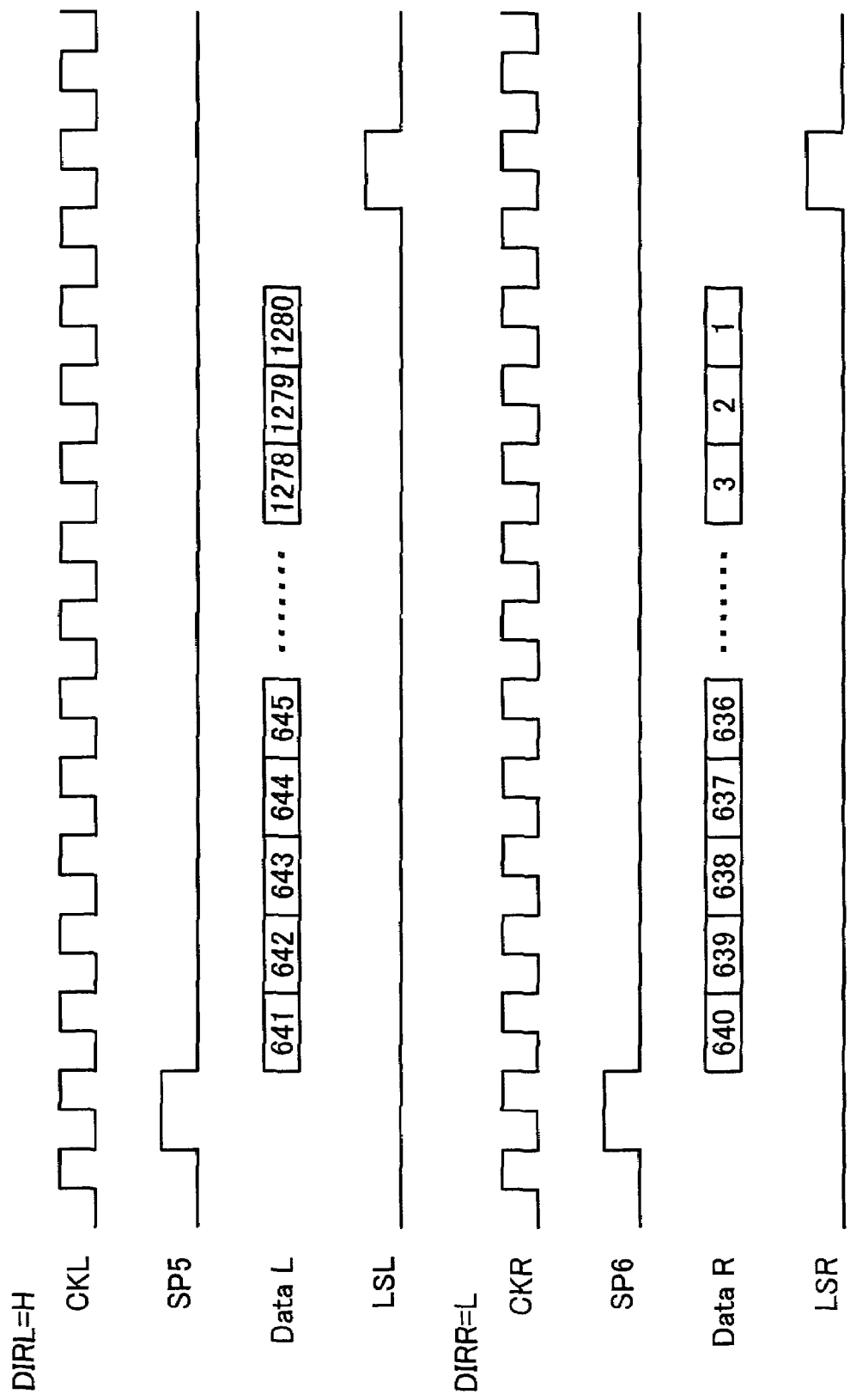
FIG. 8 is a timing chart showing signals from different sections and sequential orders of display data sent to source drivers in the liquid crystal display device which carries out left-and-right inverted display shown in FIG. 7.

On the other hand, sets of display data of each horizontal line in the left panel section 11a are sent to the source drivers SD11 through SD15 in accordance with a sequence of data641, data642, . . . data1280 (see FIG. 8). Sets of display data of each horizontal line in the right panel section 11b are sent to the source drivers. SD16 through SD20 in accordance with a sequence of data640, data639, . . . , data1 (see FIG. 8). This makes it possible to carry out normal left-and-right inverted display having a left-and-right reversed image.

FIG. 8 is a timing chart of the respective signals for carrying out left-and-right inverted display. In FIG. 8, the same codes are used for CKL, SP5, DataL, LSL, CKR, SP6, DataR, LSR, etc., as described above.

Figure 9:
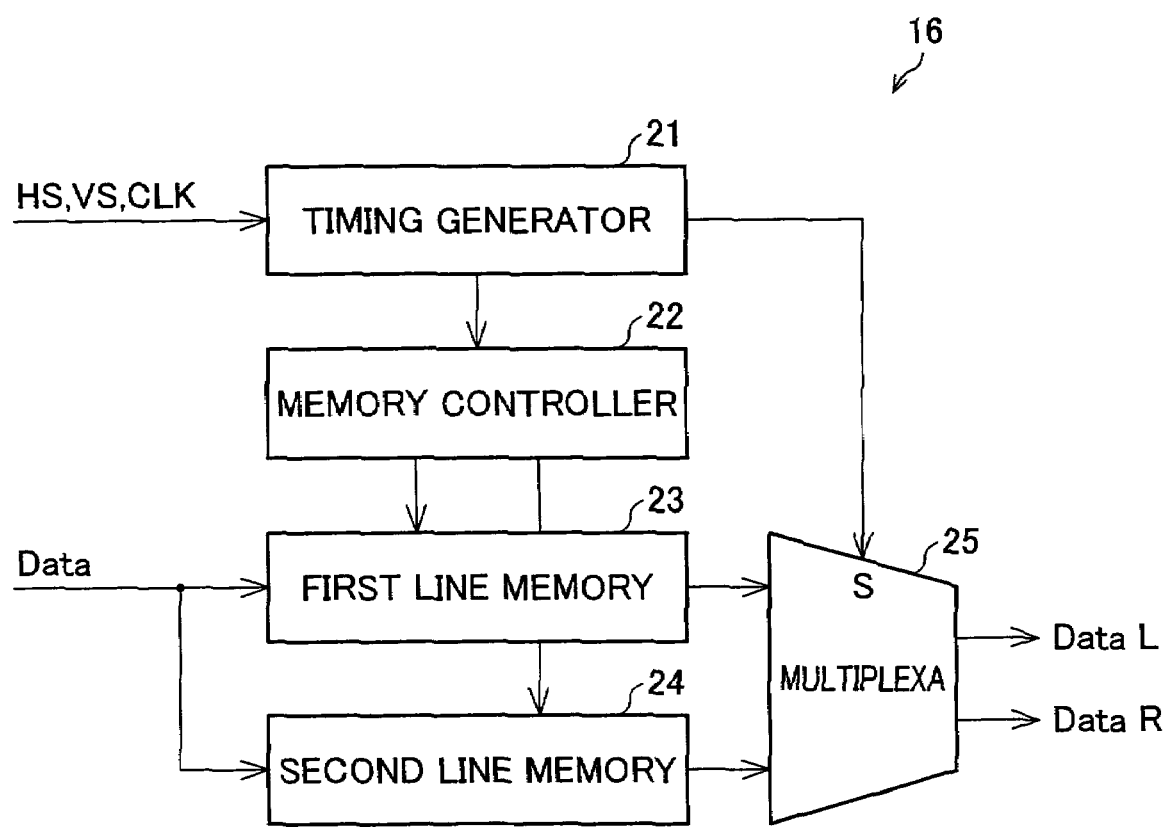
FIG. 9 is a block diagram showing a structure provided in the controller shown in FIG. 1 for sending display data to source drivers.

With reference to FIGS. 9 and 10, the following describes an exemplary structure of the controller 16 for sending display data to the source drivers SD11 through SD20.

As shown in FIG. 9, the controller 16 includes a timing generator 21, a memory controller 22, a first line memory 23, a second line memory 24, and a multiplexer 25.

The timing generator 21 receives a horizontal synchronization signal HS, a vertical synchronization signal VS, a clock CLK, etc., and sends a timing signal for controlling the memory controller 22. Based on the timing signal sent from the timing generator 21, the memory controller 22 controls operations for writing in and reading from the first line memory 23 and the second line memory 24. The multiplexer 25 obtains display data from either the first line memory 23 or the second line memory 24, and sends the display data to the source drivers SD11 through SD20.

According to the arrangement, sets of display data of the first horizontal line and display data of the second horizontal line are first written into the first line memory 23 and the second line memory 24, respectively. A sequence of these sets of display data is data1, data2, . . . , data1280 as shown in FIG. 10.

Next, display data is read from the first line memory 23 and sent to the source drivers SD11 to SD20 through the multiplexer 25, as display data for the first horizontal line. Then, as display data of the second horizontal line, sets of display data are read from the second line memory 24 and sent to the source drivers SD11 through SD20 via the multiplexer 25. While the display data are read from the second line memory 24, sets of display data for a third line are written into the first line memory 23. Next, the sets of display data for the third line are read from the first line memory 23 and sent to the source drivers SD11 through SD20 via the multiplexer 25. While the display data are read from the first line memory 23, sets of display data for a fourth line are written into the second line memory 24. In a similar manner, operations for writing and reading display data in and from the first line memory 23 and the second line memory 24 are repeated.

FIG. 10 illustrates operations for reading display data from the first line memory 23 and the second line memory 24. In regular display mode, sets of display data for the source drivers SD11 through SD15 in the left panel section 11a are read in accordance with a sequence of display data640, data639, . . . , data1, while sets of display data for the source drivers SD16 through SD20 in the right display panel section 11b are read in accordance with a sequence of display data641, data642, . . . , data1280. In left-and-right inverted display mode, sets of display data for the source drivers SD11 through SD15 in the left panel section 11a are read in accordance with a sequence of display data641, data642, . . . , data1280, while sets of display data for the source drivers SD16 through SD20 in the right display panel section 11b are read in accordance with a sequence of display data640, data639, . . . , data1.

As described above, when the liquid crystal display device with a two-split drive carries out regular display and left-and-right inverted display, start pulses SP are sent to the source drivers closest to the controller 16; the source driver SD15 in the left panel section 11a and the source driver SD16 in the right panel section 11b. Then, the operation of acquiring sets of display data sequentially shifts from the central source drivers SD15 and SD16 receiving the start pulses SP toward the source drivers SD11 and SD20 at end sides.

As described above, when the start pulses SP are sent to the source drivers SD15 and SD16 at the central region, the following occurs. In regular display mode, a sequence of display data to be supplied to the source drivers SD11 through SD15 in the left panel section 11a is in reverse order of display data to be written in a line memory. In left-and-right inverted display mode, the order of a sequence of display data to be supplied to the source drivers SD11 through SD15 in the left panel section 11a is identical with the order of display data to be supplied to the source drivers SD16 through SD20 in the right panel section 11b for carrying out regular display. Also, the order of a sequence of display data to be supplied to the source drivers SD16 through SD20 in the right panel section 11b is identical with the order of display data to be supplied to the source drivers SD11 through SD15 in the left panel section 11a for carrying out regular display.

This facilitates adjusting timings for sending both the transmission clock and the start pulse SP from the controller 6, in both regular display and left-and-right inverted display modes.

Further, the controller 16 is preferably provided in the center region of the border between the left panel section 11a and the right panel section 11b. However, this is not the only possibility. That is, the controller 16 may be provided so that at least a portion of the controller 16 is overlapped with the aforesaid border in a direction of source bus lines, for example. Further, the controller 16 may be provided so that at least a portion of the controller 16 is overlapped with either the central source driver SD15 or SD16 in the direction of the source bus lines.

According to the arrangement of the present embodiment, a liquid crystal display device with a two-split drive is described as an example. However, the present embodiment can be applied for display devices with a four-split drive or more, which requires combinations of a plurality of the two-split drives of the present embodiment.

In the liquid crystal display device of the present embodiment, scanning direction signals DIRL and DIRR are sent from the controller 16 to the source drivers SD11 through SD15 and SD16 through SD20. However, in both regular display and left-and-right inverted display modes, the start pulses SP are sent to one source driver SD, and the orders of operations of the source drivers SD acquiring the display data are identical to each other. Therefore, neither scanning direction signals DIRL nor DIRR is required to be sent from the controller 16 to the source drivers SD.

As described above, in the display device of the present invention, the controlling circuit sending the start signals to the two driving circuits closest to a border between the two display regions, and at a time of supplying the data signals, the controlling circuit rearranging an order of data signals, which are supplied to at least one of the display regions, to be in line with an order of data signals which are supplied to the other one of the display regions.

Further, in the driving method for the display device of the present invention, the start signals being sent to the two driving circuits closest to a border between the two display regions, and an order of the data signals supplied to at least one of the display regions being rearranged to be in line with an order of data signals which are supplied to the other one of the display regions.

This makes it possible to send start signals to driving circuits which are closest to the border between the first and the second display regions through a shortest transmission distance, so that the amount of retardation of start pulses are suppressed and the amount of retardation of start signals sent to the two driving circuits are equalized. Thus, it is possible to facilitate adjusting phases between other controlling signals and start signals, which are sent to the driving circuits. That is, timings for sending signals to driving circuits can be easily adjusted under a structure of a two-split drive.

In the display device, left-and-right inverted display with left-and-right inversion can be carried out, and the controlling circuit sends, in carrying out left-and-right inverted display, the start signals to the two driving circuits as in a case of carrying out regular display with no left-and-right inversion, and rearranges an order of the data signals, which are supplied to the driving circuits of the both display regions, to be in line with an order of the data signals supplied to the other one of the display regions and also in accordance with the left-and-right inverted display.

In the driving method for the display device, when carrying out left-and-right inverted display with left-and-right inversion, the start signals are sent to the two driving circuits as in case of carrying out regular display with no left-and-right inversion, and the data signals are supplied to the driving circuits of the both display regions, and an order of the data signals are rearranged to be in line with an order of the data signals supplied to the other one of display regions and to carry out left-and-right inverted display.

In this case, the display device and the driving method for the display device includes signal lines supplying the start signals from the controlling circuit to the two driving circuits, the signal lines provided only between the two driving circuits closest to the border of the two display regions and to the controlling circuit, and a number of controlling signal lines being smaller by one or more compared to a number of controlling signal lines in a conventional system in which a driving circuit for receiving a start signal in regular display mode is different from a driving circuit for receiving the start signal in left-and-right inverted display mode.

According to the arrangement, compared to the conventional system having different driving circuits for receiving start signals in regular display and left-and-right inverted display modes, the number of signal lines for sending start signals can be reduced by one or more, because one driving circuit receives start signals both in regular display and left-and-right inverted display modes. This makes it possible to reduce the number of connector pins for connecting a controlling circuit substrate and a driving circuit substrate (e.g. source substrate). Further, wiring regions for the driving circuit substrate can be downsized, so that costs are lowered. Also, in regular display and left-and-right inverted display modes, start signals are sent to one driving circuit, and the orders of operations of the driving circuits acquiring the display data are identical to each other. Thus, it is not necessary to input, to the driving circuits, a signal for specifying an order for acquiring data signals.

In the display device, the controlling circuit is shared by the first and the second display regions, and provided so that, in a direction of the data signal lines, a portion of at least one of the two driving circuits receiving the start signals in the two display regions is overlapped with a portion of the controlling circuit.

According to the arrangement, the controlling circuit is provided quite closely to the two driving circuits receiving start signals. Thus, it is suitable for reducing a transmission distance for sending start pulses.

In the display device, the respective driving circuits send data signals to data signal lines simultaneously, based on output instruction signals sent from the control device. That is, line-sequential drive is carried out.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:

1. A display device, comprising:
   a first display region;
   a second display region;
   a plurality of driving circuits which are provided along a sequence of data signal lines and correspond to the display regions; and
   a controlling circuit configured to send data signals to the respective driving circuits in parallel while sending a start signal to one of the driving circuits in each of the display regions, the plurality of driving circuits being configured so that in each of the display regions an operation of acquiring data signals corresponding to driving circuits sequentially shifting from said one of the driving circuits having received the start signal to a driving circuit next to said one of the driving circuits,
   the first display region and the second display region being provided adjacently along a sequence of a plurality of data signal lines,
   the controlling circuit being configured to send the start signals to the two driving circuits closest to a border between the two display regions, and at a time of supplying the data signals, the controlling circuit being configured to rearrange an order of data signals, which are supplied to at least one of the display regions, to be in line with an order of data signals which are supplied to the other one of the display regions,
   wherein left-and-right inverted display with left-and-right inversion can be carried out, and
   wherein the controlling circuit is configured to sends, in carrying out left-and-right inverted display, the start signals to the two driving circuits as in a case of carrying out regular display with no left-and-right inversion, and to rearrange an order of the data signals, which are supplied to the driving circuits of the both display regions, to be in line with an order of the data signals supplied to the other one of the display regions and also in accordance with the left-and-right inverted display.

2. The display device according to claim 1, further comprising: signal lines configured to supply the start signals from the controlling circuit to the two driving circuits, the signal lines provided only between the two driving circuits closest to the border of the two display regions and to the controlling circuit, and
   a number of controlling signal lines being smaller by one or more compared to a number of controlling signal lines in a conventional system in which a driving circuit for receiving a start signal in regular display mode is different from a driving circuit for receiving the start signal in left-and-right inverted display mode.

3. The display device according to claim 1, wherein the controlling circuit is shared by the first and the second display regions, and provided so that, in a direction of the data signal lines, a portion of at least one of the two driving circuits receiving the start signals in the two display regions is overlapped with a portion of the controlling circuit.

4. The display device according to claim 1, wherein the respective driving circuits are configured to send data signals to data signal lines simultaneously, based on output instruction signals sent from the control device.

5. A display device, comprising:
   a first display region;
   a second display region;
   a plurality of driving circuits which are provided along a sequence of data signal lines and correspond to the display regions; and
   a controlling circuit configured to send data signals to the respective driving circuits in parallel while sending a start signal to one of the driving circuits in each of the display regions, the plurality of driving circuits being configured so that in each of the display regions an operation of acquiring data signals corresponding to driving circuits sequentially shifting from said one of the driving circuits having received the start signal to a driving circuit next to said one of the driving circuits,
   the first display region and the second display region being provided adjacently along a sequence of a plurality of data signal lines,
   the controlling circuit being configured to send the start signals to the two driving circuits closest to a border between the two display regions, and at a time of supplying the data signals, the controlling circuit being configured to rearrange an order of data signals, which are supplied to at least one of the display regions, to be in line with an order of data signals which are supplied to the other one of the display regions
   wherein the controlling circuit has a first line memory, a second line memory, and a memory controller, and the first line memory and the second line memory store display data of a single horizontal line, and the memory controller is configured to controls operations for writing and reading display data in and from the first and second line memories.

6. The display device according to claim 5, wherein the memory controller is configured to sequentially writes and reads display data of a single horizontal line in and from the first line memory and the second line memory, and, in accordance with the regular display or the left-and-right inverted display mode, the memory controller is configured to reads out display data from the line memories, by rearranging an order of the data signals, which are supplied to the driving circuits in at least one of the display regions, to be in line with an order of data signals supplied to the other display region.

7. The display device according to claim 5, wherein the controlling circuit is shared by the first and the second display regions, and provided so that, in a direction of the data signal lines, a portion of at least one of the two driving circuits receiving the start signals in the two display regions is overlapped with a portion of the controlling circuit.

8. The display device according to claim 5, wherein the respective driving circuits are configured to send data signals to data signal lines simultaneously, based on output instruction signals sent from the control device.

9. A driving method for a display device which includes a first display region, a second display region, and a plurality of driving circuits which are provided along a sequence of data signal lines and correspond to the display regions, the first display region and the second display region being provided adjacently along a sequence of a plurality of the data signal lines, the driving circuits receiving data signals in parallel and one of the driving circuits in each of the display regions receiving a start signal, in each of the display regions an operation of acquiring data signals corresponding to driving circuits sequentially shifting from said one of the driving circuits having received the start signals to a driving circuit next to said one of the driving circuits,
   the start signals being sent to the two driving circuits closest to a border between the two display regions, and
   an order of the data signals supplied to at Least one of the display regions being rearranged to be in line with an order of data signals which are supplied to the other one of the display regions,
   wherein, when carrying out left-and-right inverted display with left-and-right inversion, the start signals are sent to the two driving circuits as in case of carrying out regular display with no left-and-right inversion, and
   wherein the data signals are supplied to the driving circuits of the both display regions, and an order of the data signals are rearranged to be in line with an order of the data signals supplied to the other one of display regions and to carry out left-and-right inverted display.

10. The driving method for a display device according to claim 9, wherein signal lines for supplying the start signals from the controlling circuit to the two driving circuits are provided only between the two driving circuits closest to the border of the two display regions and to the controlling circuit, and wherein a number of controlling signal lines is smaller by one or more compared to a number of controlling signal lines in a conventional system having different driving circuits for receiving start signals in regular display mode and in left-and-right inverted display mode.

* * * * *